United States Patent
Keyer et al.

(10) Patent No.: US 10,154,859 B2
(45) Date of Patent: *Dec. 18, 2018

(54) POLYAXIAL BOTTOM-LOADING SCREW AND ROD ASSEMBLY

(71) Applicant: DePuy Synthes Products, Inc., Raynham, MA (US)

(72) Inventors: Thomas Keyer, West Chester, PA (US); Eric McDivitt, Schwenksville, PA (US); Joseph Capozzoli, Mount Laurel, NJ (US); Boyd A. Wolf, Roswell, GA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/084,662

(22) Filed: Mar. 30, 2016

(65) Prior Publication Data

US 2016/0206350 A1    Jul. 21, 2016

Related U.S. Application Data

(63) Continuation of application No. 13/121,549, filed as application No. PCT/US2009/058788 on Sep. 29, 2009, now Pat. No. 9,320,546.

(Continued)

(51) Int. Cl.
*A61B 17/70* (2006.01)
*A61B 17/68* (2006.01)

(52) U.S. Cl.
CPC ...... *A61B 17/7037* (2013.01); *A61B 17/7007* (2013.01); *A61B 2017/681* (2013.01)

(58) Field of Classification Search
CPC ............ A61B 17/7041; A61B 17/7035; A61B 17/7032; A61B 17/7034; A61B 17/7043; A61B 17/7049

See application file for complete search history.

(56) References Cited

U.S. PATENT DOCUMENTS

| | | |
|---|---|---|
| 405,546 A | 6/1889 | Frist |
| 513,630 A | 1/1894 | Beard |

(Continued)

FOREIGN PATENT DOCUMENTS

| | | |
|---|---|---|
| CA | 2289629 | 11/1998 |
| CN | 102368967 A | 3/2012 |

(Continued)

OTHER PUBLICATIONS

International Patent Application No. PCT/US2010/031178: International Search Report dated Jun. 22, 2010, 8 pages.

(Continued)

*Primary Examiner* — Julianna N Harvey
(74) *Attorney, Agent, or Firm* — Baker & Hostetler LLP

(57) ABSTRACT

An anchor assembly for use in spinal fixation to interconnect a longitudinal spinal rod, which is integrally formed with a body of the anchor assembly. The anchor assembly includes a bone anchor, a collet, a body portion, a rod portion, and a locking cap. The anchor assembly is preferably configured so that in use, the bone anchor may be secured to the patient's vertebra prior to being received within the body portion. The anchor assembly enables a surgeon to implant the bone anchor without the body portion to maximize visibility and access around the anchoring site. Once the bone anchor has been secured to the patient's vertebra, the rod portion may be inserted into the rod-receiving channel of a second bone fixation element having a rod-receiving channel implanted at a second site and the body portion can be snapped-onto the bone anchor.

18 Claims, 9 Drawing Sheets

Related U.S. Application Data

(60) Provisional application No. 61/100,843, filed on Sep. 29, 2008.

(56) References Cited

U.S. PATENT DOCUMENTS

| | | |
|---|---|---|
| 802,896 A | 10/1905 | Webb |
| 2,005,348 A | 6/1935 | Michell |
| 2,338,659 A | 1/1944 | Morehouse |
| 2,396,925 A | 3/1946 | Morehouse |
| 3,173,987 A | 3/1965 | Potruch |
| 3,463,427 A | 8/1969 | Fisher |
| 4,447,934 A | 5/1984 | Anscher |
| 4,601,491 A | 7/1986 | Bell, Jr. et al. |
| 4,719,905 A | 1/1988 | Steffee |
| 4,805,602 A | 2/1989 | Puno et al. |
| 4,846,614 A | 7/1989 | Steinbock |
| 4,863,383 A | 9/1989 | Grafelmann |
| 4,936,851 A | 6/1990 | Fox |
| 4,944,475 A | 7/1990 | Ono et al. |
| 4,946,458 A | 8/1990 | Harms et al. |
| 5,005,562 A | 4/1991 | Cotrel |
| 5,116,337 A | 5/1992 | Johnson |
| 5,129,388 A | 7/1992 | Vignaud et al. |
| 5,207,678 A | 5/1993 | Harms et al. |
| 5,242,446 A | 9/1993 | Steffee et al. |
| 5,270,678 A | 12/1993 | Gambut et al. |
| 5,282,825 A | 2/1994 | Muck et al. |
| 5,304,178 A | 4/1994 | Stahurski |
| 5,306,275 A | 4/1994 | Bryan |
| 5,306,285 A | 4/1994 | Bryan |
| 5,312,410 A | 5/1994 | Miller et al. |
| 5,360,431 A | 11/1994 | Puno et al. |
| 5,383,882 A | 1/1995 | Buess et al. |
| 5,395,374 A | 3/1995 | Miller et al. |
| 5,413,576 A | 5/1995 | Rivard |
| 5,413,602 A | 5/1995 | Metz-Stavenhagen |
| 5,417,684 A | 5/1995 | Jackson et al. |
| 5,443,467 A | 8/1995 | Biedermann |
| 5,449,361 A | 9/1995 | Preissman |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,464 A | 12/1995 | Metz-Stavenhagen et al. |
| 5,486,174 A | 1/1996 | Fournet-Fayard et al. |
| 5,496,321 A | 3/1996 | Puno et al. |
| 5,498,262 A | 3/1996 | Bryan |
| 5,501,684 A | 3/1996 | Schlapfer et al. |
| 5,520,689 A | 5/1996 | Schlaepfer et al. |
| 5,520,690 A | 5/1996 | Errico et al. |
| 5,527,183 A | 6/1996 | O'Brien |
| 5,531,746 A | 7/1996 | Errico et al. |
| 5,534,001 A | 7/1996 | Schlapfer et al. |
| 5,536,268 A | 7/1996 | Griss |
| 5,536,270 A | 7/1996 | Songer et al. |
| 5,540,698 A | 7/1996 | Preissman et al. |
| 5,549,608 A | 8/1996 | Errico et al. |
| 5,549,677 A | 8/1996 | Durr |
| 5,554,157 A | 9/1996 | Errico et al. |
| 5,562,661 A | 10/1996 | Yoshimi et al. |
| 5,575,792 A | 11/1996 | Errico et al. |
| 5,578,033 A | 11/1996 | Errico et al. |
| 5,584,832 A | 12/1996 | Schlaepfer |
| 5,584,834 A | 12/1996 | Errico et al. |
| 5,586,984 A | 12/1996 | Errico et al. |
| 5,601,261 A | 2/1997 | Koike |
| 5,601,429 A | 2/1997 | Blacklock |
| 5,605,457 A | 2/1997 | Bailey et al. |
| 5,605,458 A | 2/1997 | Bailey et al. |
| 5,607,304 A | 3/1997 | Bailey et al. |
| 5,607,426 A | 3/1997 | Ralph et al. |
| 5,609,593 A | 3/1997 | Errico et al. |
| 5,609,594 A | 3/1997 | Errico et al. |
| 5,624,442 A | 4/1997 | Mellinger et al. |
| 5,643,262 A | 7/1997 | Metz-Stavenhagen et al. |
| 5,643,265 A | 7/1997 | Errico et al. |
| 5,645,544 A | 7/1997 | Tai et al. |
| 5,647,873 A | 7/1997 | Errico et al. |
| 5,662,651 A | 9/1997 | Tornier et al. |
| 5,667,508 A | 9/1997 | Errico et al. |
| 5,669,911 A | 9/1997 | Errico et al. |
| 5,672,175 A | 9/1997 | Martin |
| 5,683,390 A | 11/1997 | Metz-Stavenhagen et al. |
| 5,683,392 A | 11/1997 | Richelsoph et al. |
| 5,683,404 A | 11/1997 | Johnson |
| 5,688,273 A | 11/1997 | Errico et al. |
| 5,690,630 A | 11/1997 | Errico et al. |
| 5,694,760 A | 12/1997 | Baxter |
| 5,704,939 A | 1/1998 | Justin |
| 5,725,582 A | 3/1998 | Bevan et al. |
| 5,725,588 A | 3/1998 | Errico et al. |
| 5,728,098 A | 3/1998 | Sherman et al. |
| 5,733,285 A | 3/1998 | Errico et al. |
| 5,738,685 A | 4/1998 | Halm et al. |
| 5,772,663 A | 6/1998 | Whiteside et al. |
| 5,782,831 A | 7/1998 | Sherman et al. |
| 5,782,833 A | 7/1998 | Haider |
| 5,797,911 A | 8/1998 | Sherman et al. |
| 5,810,818 A | 9/1998 | Errico et al. |
| 5,817,094 A | 10/1998 | Errico et al. |
| 5,860,987 A | 1/1999 | Ratcliff et al. |
| 5,863,293 A | 1/1999 | Richelsoph |
| 5,868,748 A | 2/1999 | Burke |
| 5,876,402 A | 3/1999 | Errico et al. |
| 5,879,350 A * | 3/1999 | Sherman ............ A61B 17/7037 606/266 |
| 5,882,350 A | 3/1999 | Ralph et al. |
| 5,885,286 A | 3/1999 | Sherman et al. |
| 5,888,204 A | 3/1999 | Ralph et al. |
| 5,891,145 A | 4/1999 | Morrison et al. |
| 5,899,940 A | 5/1999 | Carchidi |
| 5,902,305 A | 5/1999 | Beger |
| 5,938,663 A | 8/1999 | Petreto |
| 5,951,287 A | 9/1999 | Hawkinson |
| 5,961,329 A | 10/1999 | Stucki-McCormick |
| 5,964,760 A | 10/1999 | Richelsoph |
| 6,001,098 A | 12/1999 | Metz-Stavenhagen et al. |
| 6,010,503 A | 1/2000 | Richelsoph et al. |
| 6,015,409 A | 1/2000 | Jackson |
| 6,017,177 A | 1/2000 | Lanham |
| 6,019,760 A | 2/2000 | Metz-Stavenhagen et al. |
| 6,022,350 A | 2/2000 | Ganem |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlaepfer et al. |
| 6,077,263 A | 6/2000 | Ameil et al. |
| 6,083,224 A | 7/2000 | Gertzbein et al. |
| 6,090,110 A | 7/2000 | Metz-Stavenhagen |
| 6,126,662 A | 10/2000 | Carmichael |
| 6,132,432 A | 10/2000 | Richelsoph |
| 6,183,472 B1 | 2/2001 | Lutz |
| 6,214,006 B1 | 4/2001 | Metz-Stavenhagen |
| 6,217,331 B1 | 4/2001 | Rogers |
| 6,224,598 B1 | 5/2001 | Jackson |
| 6,248,105 B1 | 6/2001 | Schlapfer et al. |
| 6,261,287 B1 | 7/2001 | Metz-Stavenhagen |
| 6,273,914 B1 | 8/2001 | Papas |
| 6,280,442 B1 | 8/2001 | Barker et al. |
| 6,296,642 B1 | 10/2001 | Morrison et al. |
| 6,325,802 B1 | 12/2001 | Frigg |
| 6,355,040 B1 | 3/2002 | Richelsoph et al. |
| 6,361,535 B2 | 3/2002 | Jackson |
| RE37,665 E | 4/2002 | Ralph et al. |
| 6,368,321 B1 | 4/2002 | Jackson |
| 6,402,752 B2 | 6/2002 | Schaffler-Wachter et al. |
| 6,440,132 B1 | 8/2002 | Jackson |
| 6,443,953 B1 | 9/2002 | Perra et al. |
| 6,451,021 B1 | 9/2002 | Ralph et al. |
| 6,454,768 B1 | 9/2002 | Jackson |
| 6,454,772 B1 | 9/2002 | Jackson |
| 6,471,705 B1 | 10/2002 | Biedermann et al. |
| 6,482,207 B1 | 11/2002 | Errico |
| 6,485,491 B1 | 11/2002 | Farris et al. |
| 6,491,696 B1 | 12/2002 | Kunkel |

(56) References Cited

U.S. PATENT DOCUMENTS

| | | |
|---|---|---|
| 6,508,820 B2 | 1/2003 | Bales |
| 6,514,255 B1 | 2/2003 | Ferree |
| 6,520,963 B1 | 2/2003 | McKinley |
| 6,533,226 B2 | 3/2003 | Geiger |
| 6,537,070 B1 | 3/2003 | Stucki-McCormick |
| 6,537,276 B2 | 3/2003 | Metz-Stavenhagen |
| 6,554,831 B1 | 4/2003 | Rivard et al. |
| 6,558,387 B2 | 5/2003 | Errico et al. |
| 6,565,565 B1 | 5/2003 | Yuan et al. |
| 6,585,740 B2 | 7/2003 | Schlapfer et al. |
| 6,616,667 B1 | 9/2003 | Steiger et al. |
| 6,626,908 B2 | 9/2003 | Wilson et al. |
| 6,641,586 B2 | 11/2003 | Wilson |
| 6,641,588 B2 | 11/2003 | Citron et al. |
| 6,660,004 B2 | 12/2003 | Barker et al. |
| 6,689,140 B2 | 2/2004 | Cohen |
| 6,695,852 B2 | 2/2004 | Gleason |
| 6,716,214 B1 | 4/2004 | Jackson |
| 6,726,687 B2 | 4/2004 | Jackson |
| 6,736,820 B2 | 5/2004 | Biedermann et al. |
| 6,738,527 B2 | 5/2004 | Kuwata et al. |
| 6,740,086 B2 | 5/2004 | Richelsoph |
| 6,749,613 B1 | 6/2004 | Conchy et al. |
| 6,755,829 B1 | 6/2004 | Bono et al. |
| 6,770,075 B2 | 8/2004 | Howland |
| 6,780,186 B2 | 8/2004 | Errico et al. |
| 6,783,527 B2 | 8/2004 | Drewry et al. |
| 6,802,844 B2 | 10/2004 | Ferree |
| 6,827,719 B2 | 12/2004 | Ralph et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,869,433 B2 | 3/2005 | Glascott |
| 6,887,275 B2 | 5/2005 | Carchidi |
| 6,933,440 B2 | 8/2005 | Ichikawa et al. |
| 6,964,666 B2 | 11/2005 | Jackson |
| 6,974,460 B2 | 12/2005 | Carbone et al. |
| 6,981,973 B2 | 1/2006 | McKinley |
| 7,008,227 B2 | 3/2006 | Carmichael |
| 7,018,378 B2 | 3/2006 | Biedermann et al. |
| RE39,089 E | 5/2006 | Ralph et al. |
| 7,073,415 B2 | 7/2006 | Casutt et al. |
| 7,081,117 B2 | 7/2006 | Bono et al. |
| 7,087,057 B2 | 8/2006 | Konieczynski et al. |
| D527,678 S | 9/2006 | Warner |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,131,467 B2 | 11/2006 | Gao et al. |
| 7,144,396 B2 | 12/2006 | Shluzas |
| 7,163,539 B2 | 1/2007 | Abdelgany et al. |
| 7,175,622 B2 | 2/2007 | Farris |
| 7,186,255 B2 | 3/2007 | Baynham et al. |
| 7,211,086 B2 | 5/2007 | Biedermann et al. |
| 7,223,268 B2 | 5/2007 | Biedermann |
| 7,250,052 B2 | 7/2007 | Landry et al. |
| 7,270,665 B2 | 9/2007 | Morrison et al. |
| 7,316,684 B1 | 1/2008 | Baccelli et al. |
| 7,322,548 B2 | 1/2008 | Mielke et al. |
| 7,330,490 B2 | 2/2008 | Furukawa et al. |
| 7,338,490 B2 | 3/2008 | Ogilvie et al. |
| 7,445,627 B2 | 11/2008 | Hawkes et al. |
| 7,452,360 B2 | 11/2008 | Trudeau et al. |
| 7,476,239 B2 | 1/2009 | Jackson |
| 7,547,319 B2 | 6/2009 | Segal et al. |
| 7,591,839 B2 | 9/2009 | Biedermann et al. |
| 7,592,546 B2 | 9/2009 | Johansson |
| 7,645,282 B2 | 1/2010 | Huxel et al. |
| 7,648,520 B2 | 1/2010 | Markworth |
| 7,691,131 B2 | 4/2010 | Graf |
| 7,708,762 B2 | 5/2010 | McCarthy et al. |
| 7,766,944 B2 | 8/2010 | Metz-Stavenhagen |
| 7,780,706 B2 | 8/2010 | Marino |
| 7,785,352 B2 | 8/2010 | Snyder et al. |
| 7,785,354 B2 | 8/2010 | Biedermann |
| 7,799,054 B2 | 9/2010 | Kwak et al. |
| 7,803,174 B2 | 9/2010 | Francis et al. |
| 7,806,895 B2 | 10/2010 | Weier et al. |
| 7,819,902 B2 | 10/2010 | Abdelgany et al. |
| 7,951,172 B2 | 5/2011 | Chao et al. |
| 7,967,849 B2 | 6/2011 | Carson et al. |
| 8,001,946 B2 | 8/2011 | Leitl |
| 8,002,806 B2 | 8/2011 | Justis |
| 8,029,513 B2 | 10/2011 | Konno et al. |
| 8,029,546 B2 | 10/2011 | Capote et al. |
| 8,038,701 B2 | 10/2011 | Rock et al. |
| 8,096,998 B2 | 1/2012 | Cresina |
| 8,100,946 B2 | 1/2012 | Strausbaugh et al. |
| 8,137,356 B2 | 3/2012 | Hestad et al. |
| 8,172,772 B2 | 5/2012 | Zwolinski et al. |
| 8,197,517 B1 | 6/2012 | Lab et al. |
| 8,216,245 B2 | 7/2012 | Gil et al. |
| 8,221,464 B2 | 7/2012 | Belliard et al. |
| 8,231,626 B2 | 7/2012 | Hulliger et al. |
| 8,241,333 B2 | 8/2012 | Jackson |
| 8,246,659 B2 | 8/2012 | Vonwiller et al. |
| 8,257,367 B2 | 9/2012 | Bryant et al. |
| 8,308,782 B2 | 11/2012 | Jackson |
| 8,317,836 B2 | 11/2012 | Zucherman et al. |
| 8,323,318 B2 | 12/2012 | Baccelli et al. |
| 8,444,681 B2 | 5/2013 | Jackson et al. |
| 8,469,960 B2 | 6/2013 | Hutton et al. |
| 8,469,966 B2 | 6/2013 | Allen et al. |
| 8,556,938 B2 | 10/2013 | Jackson et al. |
| 8,628,558 B2 | 1/2014 | Harvey et al. |
| 8,632,572 B2 | 1/2014 | Darst Rice et al. |
| 8,663,298 B2 | 3/2014 | Keyer et al. |
| 8,814,910 B2 | 8/2014 | Baccelli et al. |
| 8,840,652 B2 | 9/2014 | Jackson |
| 8,870,869 B2 | 10/2014 | Meunier et al. |
| 8,870,870 B2 | 10/2014 | Baccelli et al. |
| 8,882,803 B2 | 11/2014 | Iott et al. |
| 8,911,478 B2 | 12/2014 | Jackson et al. |
| 8,911,479 B2 | 12/2014 | Jackson et al. |
| 8,926,672 B2 | 1/2015 | Jackson et al. |
| 8,979,904 B2 | 3/2015 | Jackson et al. |
| 8,998,959 B2 | 4/2015 | Jackson et al. |
| 8,998,961 B1 | 4/2015 | Ziemek et al. |
| 9,039,708 B2 | 5/2015 | Larroque-Lahitette |
| 9,168,069 B2 | 10/2015 | Jackson et al. |
| 9,216,041 B2 | 12/2015 | Jackson et al. |
| 9,320,546 B2 | 4/2016 | Keyer et al. |
| 9,326,796 B2 | 5/2016 | Harvey et al. |
| 9,393,047 B2 | 7/2016 | Jackson et al. |
| 9,439,681 B2 | 9/2016 | Keyer et al. |
| 9,451,993 B2 | 9/2016 | Jackson et al. |
| 9,480,517 B2 | 11/2016 | Jackson et al. |
| 9,504,496 B2 | 11/2016 | Jackson et al. |
| 9,522,021 B2 | 12/2016 | Jackson et al. |
| 9,636,146 B2 | 5/2017 | Jackson et al. |
| 9,717,533 B2 | 8/2017 | Jackson et al. |
| 9,717,534 B2 | 8/2017 | Jackson et al. |
| 2001/0047173 A1 | 11/2001 | Schlapfer et al. |
| 2002/0045899 A1 | 4/2002 | Errico et al. |
| 2002/0068940 A1 | 6/2002 | Gaines |
| 2002/0069537 A1 | 6/2002 | Wenzler |
| 2002/0103487 A1 | 8/2002 | Errico et al. |
| 2002/0117321 A1 | 8/2002 | Beebe et al. |
| 2002/0120272 A1 | 8/2002 | Yuan et al. |
| 2002/0138077 A1 | 9/2002 | Ferree |
| 2002/0143341 A1 | 10/2002 | Biedermann et al. |
| 2002/0151900 A1 | 10/2002 | Glascott |
| 2003/0100896 A1 | 5/2003 | Biedermann et al. |
| 2003/0100904 A1 | 5/2003 | Biedermann |
| 2003/0125741 A1 | 7/2003 | Biedermann et al. |
| 2003/0125742 A1 | 7/2003 | Yuan et al. |
| 2003/0149431 A1 | 8/2003 | Varieur |
| 2003/0153912 A1 | 8/2003 | Graf |
| 2004/0006342 A1 | 1/2004 | Altarac et al. |
| 2004/0024464 A1 | 2/2004 | Errico et al. |
| 2004/0039384 A1 | 2/2004 | Boehm et al. |
| 2004/0111088 A1 | 6/2004 | Picetti et al. |
| 2004/0138660 A1 | 7/2004 | Serhan |
| 2004/0143265 A1 | 7/2004 | Landry et al. |

(56) References Cited

U.S. PATENT DOCUMENTS

| | | |
|---|---|---|
| 2004/0153077 A1 | 8/2004 | Biedermann et al. |
| 2004/0157186 A1 | 8/2004 | Abels et al. |
| 2004/0162558 A1 | 8/2004 | Hegde et al. |
| 2004/0172022 A1 | 9/2004 | Landry et al. |
| 2004/0181224 A1 | 9/2004 | Biedermann et al. |
| 2004/0186473 A1 | 9/2004 | Cournoyer et al. |
| 2004/0186474 A1 | 9/2004 | Matthis et al. |
| 2004/0193160 A1 | 9/2004 | Richelsoph |
| 2004/0199169 A1 | 10/2004 | Koons et al. |
| 2004/0225292 A1 | 11/2004 | Sasso et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0033298 A1 | 2/2005 | Hawkes et al. |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0080415 A1 | 4/2005 | Keyer et al. |
| 2005/0080420 A1 | 4/2005 | Farris et al. |
| 2005/0143737 A1 | 6/2005 | Pafford et al. |
| 2005/0154389 A1* | 7/2005 | Selover ............ A61B 17/00234 606/914 |
| 2005/0154391 A1 | 7/2005 | Doherty |
| 2005/0171537 A1 | 8/2005 | Mazel et al. |
| 2005/0171542 A1 | 8/2005 | Biedermann et al. |
| 2005/0177154 A1 | 8/2005 | Moumene et al. |
| 2005/0177166 A1 | 8/2005 | Timm et al. |
| 2005/0177179 A1 | 8/2005 | Baynham et al. |
| 2005/0187548 A1 | 8/2005 | Butler et al. |
| 2005/0192571 A1 | 9/2005 | Abdelgany |
| 2005/0203515 A1 | 9/2005 | Doherty et al. |
| 2005/0203516 A1 | 9/2005 | Biedermann et al. |
| 2005/0209592 A1 | 9/2005 | Schlapfer et al. |
| 2005/0216001 A1 | 9/2005 | David |
| 2005/0216003 A1 | 9/2005 | Biedermann et al. |
| 2005/0228378 A1 | 10/2005 | Kalfas et al. |
| 2005/0228385 A1 | 10/2005 | Iott et al. |
| 2005/0234421 A1 | 10/2005 | Markworth |
| 2005/0234451 A1 | 10/2005 | Markworth |
| 2005/0261687 A1 | 11/2005 | Garamszegi et al. |
| 2005/0277928 A1 | 12/2005 | Boschert |
| 2005/0283157 A1 | 12/2005 | Coates et al. |
| 2005/0288671 A1 | 12/2005 | Yuan et al. |
| 2006/0004357 A1 | 1/2006 | Lee et al. |
| 2006/0025767 A1 | 2/2006 | Khalili |
| 2006/0025770 A1 | 2/2006 | Schlapfer et al. |
| 2006/0036252 A1 | 2/2006 | Baynham et al. |
| 2006/0052818 A1 | 3/2006 | Drake et al. |
| 2006/0064091 A1 | 3/2006 | Ludwig et al. |
| 2006/0079892 A1 | 4/2006 | Roychowdhury et al. |
| 2006/0084993 A1 | 4/2006 | Landry et al. |
| 2006/0084995 A1 | 4/2006 | Biedermann et al. |
| 2006/0084996 A1 | 4/2006 | Metz-Stavenhagen |
| 2006/0089634 A1 | 4/2006 | Anderson et al. |
| 2006/0089643 A1 | 4/2006 | Mujwid |
| 2006/0106383 A1 | 5/2006 | Biedermann et al. |
| 2006/0111779 A1 | 5/2006 | Petersen et al. |
| 2006/0129149 A1 | 6/2006 | Iott et al. |
| 2006/0142761 A1 | 6/2006 | Landry et al. |
| 2006/0149232 A1 | 7/2006 | Sasing |
| 2006/0149233 A1 | 7/2006 | Richelsoph |
| 2006/0149241 A1 | 7/2006 | Richelsoph et al. |
| 2006/0149265 A1 | 7/2006 | James |
| 2006/0155277 A1 | 7/2006 | Metz-Stavenhagen |
| 2006/0173456 A1 | 8/2006 | Hawkes et al. |
| 2006/0200131 A1 | 9/2006 | Chao et al. |
| 2006/0212034 A1 | 9/2006 | Triplett et al. |
| 2006/0217717 A1 | 9/2006 | Whipple |
| 2006/0229611 A1 | 10/2006 | Avery et al. |
| 2006/0235385 A1 | 10/2006 | Whipple |
| 2006/0235393 A1 | 10/2006 | Bono et al. |
| 2006/0241594 A1 | 10/2006 | McCarthy et al. |
| 2006/0241599 A1 | 10/2006 | Konieczynski et al. |
| 2006/0241624 A1 | 10/2006 | Kizuka et al. |
| 2006/0247636 A1 | 11/2006 | Yuan et al. |
| 2006/0247668 A1 | 11/2006 | Park |
| 2006/0271047 A1 | 11/2006 | Jackson |
| 2006/0293659 A1 | 12/2006 | Alvarez |
| 2006/0293664 A1 | 12/2006 | Schumacher |
| 2007/0016200 A1 | 1/2007 | Jackson |
| 2007/0043365 A1 | 2/2007 | Ritland |
| 2007/0049932 A1 | 3/2007 | Richelsoph et al. |
| 2007/0055240 A1 | 3/2007 | Matthis et al. |
| 2007/0088357 A1 | 4/2007 | Johnson |
| 2007/0090238 A1 | 4/2007 | Justis |
| 2007/0118118 A1 | 5/2007 | Kwak et al. |
| 2007/0118121 A1 | 5/2007 | Purcell et al. |
| 2007/0118123 A1 | 5/2007 | Strausbaugh et al. |
| 2007/0123860 A1 | 5/2007 | Francis et al. |
| 2007/0123870 A1 | 5/2007 | Jeon et al. |
| 2007/0135817 A1* | 6/2007 | Ensign ............... A61B 17/7007 606/96 |
| 2007/0161987 A1 | 7/2007 | Capote et al. |
| 2007/0161994 A1 | 7/2007 | Lowery et al. |
| 2007/0167949 A1 | 7/2007 | Altarac et al. |
| 2007/0179501 A1 | 8/2007 | Firkins |
| 2007/0191844 A1 | 8/2007 | Carls et al. |
| 2007/0198014 A1 | 8/2007 | Graf et al. |
| 2007/0225711 A1 | 9/2007 | Ensign |
| 2007/0233087 A1 | 10/2007 | Schlapfer |
| 2007/0246614 A1 | 10/2007 | Allmann et al. |
| 2007/0250061 A1 | 10/2007 | Chin et al. |
| 2007/0250064 A1 | 10/2007 | Darois |
| 2007/0270805 A1 | 11/2007 | Miller |
| 2007/0270817 A1 | 11/2007 | Rezach |
| 2007/0270820 A1 | 11/2007 | Dickinson et al. |
| 2007/0270880 A1 | 11/2007 | Lindemann |
| 2007/0282339 A1 | 12/2007 | Schwab |
| 2007/0288004 A1* | 12/2007 | Alvarez ............ A61B 17/7032 606/86 A |
| 2008/0039843 A1 | 2/2008 | Abdou |
| 2008/0058805 A1 | 3/2008 | Stuart |
| 2008/0058812 A1 | 3/2008 | Zehnder |
| 2008/0086126 A1 | 4/2008 | Miller |
| 2008/0103502 A1 | 5/2008 | Capote et al. |
| 2008/0140075 A1* | 6/2008 | Ensign ............... A61B 17/7007 606/60 |
| 2008/0140135 A1 | 6/2008 | Konieczynski et al. |
| 2008/0154308 A1 | 6/2008 | Sherman et al. |
| 2008/0177260 A1 | 7/2008 | McKinley et al. |
| 2008/0177323 A1 | 7/2008 | Null et al. |
| 2008/0188260 A1 | 8/2008 | Xiao et al. |
| 2008/0208257 A1 | 8/2008 | Matthys |
| 2008/0215095 A1 | 9/2008 | Biedermann et al. |
| 2008/0234743 A1 | 9/2008 | Marik |
| 2008/0243185 A1 | 10/2008 | Felix |
| 2008/0249570 A1 | 10/2008 | Carson et al. |
| 2008/0262552 A1 | 10/2008 | Kim |
| 2008/0262553 A1 | 10/2008 | Hawkins et al. |
| 2008/0269810 A1 | 10/2008 | Zhang et al. |
| 2008/0294194 A1 | 11/2008 | Capote et al. |
| 2008/0294202 A1 | 11/2008 | Peterson et al. |
| 2008/0306553 A1 | 12/2008 | Zucherman et al. |
| 2008/0312692 A1 | 12/2008 | Brennan et al. |
| 2009/0088803 A1 | 4/2009 | Justis et al. |
| 2009/0093847 A1 | 4/2009 | Wilcox |
| 2009/0105770 A1 | 4/2009 | Berrevoets |
| 2009/0149887 A1 | 6/2009 | Schlapfer et al. |
| 2009/0187217 A1 | 7/2009 | Weiman et al. |
| 2009/0198280 A1 | 8/2009 | Spratt et al. |
| 2009/0259256 A1 | 10/2009 | Miller |
| 2009/0270916 A1 | 10/2009 | Ramsay et al. |
| 2010/0004694 A1 | 1/2010 | Little |
| 2010/0042165 A1 | 2/2010 | Aflatoon |
| 2010/0057125 A1 | 3/2010 | Viker |
| 2010/0087864 A1 | 4/2010 | Klein et al. |
| 2010/0094345 A1 | 4/2010 | Saidha et al. |
| 2010/0145394 A1 | 6/2010 | Harvey et al. |
| 2010/0168797 A1 | 7/2010 | Graf |
| 2010/0191286 A1 | 7/2010 | Butler |
| 2010/0198272 A1 | 8/2010 | Keyer et al. |
| 2010/0241172 A1 | 9/2010 | Biyani et al. |
| 2010/0276051 A1 | 11/2010 | Kanehira |
| 2010/0298890 A1 | 11/2010 | Marino |

(56) References Cited

U.S. PATENT DOCUMENTS

| | | | |
|---|---|---|---|
| 2010/0298891 A1* | 11/2010 | Jackson | A61B 17/7008 606/308 |
| 2010/0305621 A1 | 12/2010 | Wang | |
| 2010/0313428 A1 | 12/2010 | Mocanu | |
| 2010/0324599 A1 | 12/2010 | Montello | |
| 2011/0106166 A1 | 5/2011 | Keyer et al. | |
| 2011/0213424 A1 | 9/2011 | Biedermann et al. | |
| 2011/0230917 A1 | 9/2011 | Carson et al. | |
| 2011/0270325 A1 | 11/2011 | Keyer et al. | |
| 2011/0276051 A1 | 11/2011 | Blakemore et al. | |
| 2012/0010629 A1 | 1/2012 | Mire et al. | |
| 2012/0089194 A1 | 4/2012 | Wolf et al. | |
| 2012/0109200 A1 | 5/2012 | Cahill et al. | |
| 2012/0265249 A1 | 10/2012 | Fielding et al. | |
| 2013/0012955 A1 | 1/2013 | Lin et al. | |
| 2013/0012995 A1 | 1/2013 | Butterfield et al. | |
| 2013/0079827 A1 | 3/2013 | Neary et al. | |
| 2013/0261680 A1 | 10/2013 | Baccelli et al. | |
| 2013/0268011 A1 | 10/2013 | Rezach et al. | |

FOREIGN PATENT DOCUMENTS

| | | |
|---|---|---|
| CN | 102458279 A | 5/2012 |
| DE | 9314297 U1 | 4/1994 |
| DE | 4329220 A1 | 9/1995 |
| DE | 29903342 U1 | 6/1999 |
| DE | 29810798 U1 | 10/1999 |
| DE | 19912364 A1 | 10/2000 |
| DE | 20207785 U1 | 9/2003 |
| EP | 0408489 A1 | 1/1991 |
| EP | 0 674 880 | 10/1995 |
| EP | 0807420 B1 | 5/1997 |
| EP | 0612507 B1 | 12/1998 |
| EP | 0683644 B1 | 6/2000 |
| EP | 1210914 A1 | 6/2002 |
| EP | 1248573 | 10/2002 |
| EP | 1 269 929 | 1/2003 |
| EP | 1294297 B1 | 3/2003 |
| EP | 1316295 A2 | 6/2003 |
| EP | 1323391 A2 | 7/2003 |
| EP | 0828459 | 9/2003 |
| EP | 0 837 656 | 12/2003 |
| EP | 1637085 | 3/2006 |
| EP | 1313403 B1 | 10/2006 |
| EP | 1 198 205 | 11/2006 |
| EP | 1741396 | 1/2007 |
| EP | 1665994 B1 | 6/2008 |
| EP | 1961392 A1 | 8/2008 |
| EP | 2052690 | 4/2009 |
| GB | 2414674 B | 8/2008 |
| JP | 06-154258 | 6/1994 |
| JP | 08-112291 A | 5/1996 |
| JP | 2005-510286 | 4/2005 |
| JP | 2006-508748 A | 3/2006 |
| JP | 2006-154258 | 6/2006 |
| JP | 2006-525102 | 11/2006 |
| JP | 2009-535114 A | 10/2009 |
| JP | 2012-523927 A | 10/2012 |
| JP | 2012-530550 A | 12/2012 |
| KR | 10-2008-0112851 A | 12/2008 |
| KR | 100896043 B1 | 5/2009 |
| KR | 10-2012-0013312 A | 2/2012 |
| KR | 10-2012-0039622 A | 4/2012 |
| WO | 94/17736 A1 | 8/1994 |
| WO | 96/32071 A1 | 10/1996 |
| WO | WO 97/02786 | 1/1997 |
| WO | WO 1998/052482 A1 | 11/1998 |
| WO | WO 00/21455 | 4/2000 |
| WO | 01/06940 A1 | 2/2001 |
| WO | 01/52758 A1 | 7/2001 |
| WO | WO 02/00124 A1 | 1/2002 |
| WO | 02/17803 A2 | 3/2002 |
| WO | WO 02/076314 A1 | 10/2002 |
| WO | WO 2003/045261 A1 | 6/2003 |
| WO | WO 2004/052218 A1 | 6/2004 |
| WO | WO 2004/089245 | 10/2004 |
| WO | WO 2004/098425 | 11/2004 |
| WO | WO 2005/016161 A1 | 2/2005 |
| WO | WO 2006/088452 A2 | 8/2006 |
| WO | 2006/114437 A1 | 11/2006 |
| WO | WO 2006/116437 | 11/2006 |
| WO | WO 2007/038350 | 4/2007 |
| WO | WO 2007/045892 A1 | 4/2007 |
| WO | WO 2007/047711 A2 | 4/2007 |
| WO | 2007/127632 A2 | 11/2007 |
| WO | WO 2007/146032 | 12/2007 |
| WO | WO 2008/027940 | 3/2008 |
| WO | WO 2008/048953 A2 | 4/2008 |
| WO | 2008/069420 A1 | 6/2008 |
| WO | WO 2008/089096 A2 | 7/2008 |
| WO | WO 2008/146185 A1 | 12/2008 |
| WO | WO 2009/001978 A1 | 12/2008 |
| WO | WO 2009/015100 | 1/2009 |
| WO | WO 2010/030906 | 3/2010 |
| WO | WO 2010/028287 A3 | 6/2010 |
| WO | WO 2010/120989 | 10/2010 |
| WO | WO 2010/148231 A1 | 12/2010 |
| WO | WO 2012/154772 A2 | 11/2012 |

OTHER PUBLICATIONS

International Patent Application No. PCT/US2010/031178: Notification of Transmittal of the International Preliminary Report on Patentability, 21 pages.
International Patent Application No. PCT/US2010/039037: International Search Report dated Jan. 9, 2010, 5 pages.
International Patent Application No. PCT/US2010/039037: International Preliminary Report on Patentability dated Jul. 11, 2011.
International Patent Application No. PCT/US2009/056692: International Search Report and Written Opinion dated Dec. 3, 2009, 14 pages.
International Patent Application No. PCT/US2008/070670: International Search Report dated Feb. 17, 2009, 3 pages.
International Patent Application No. PCT/US2008/070670: International Preliminary Report on Patentability, 6 pages.
Aebi et al., "AO ASIF Principles in Spine Surgery", Springer, 1998, 186-190.
International Patent Application No. PCT/US2006/037120: International Search Report dated Jul. 11, 2007, 4 pages.
International Patent Application No. PCT/US2006/047986: International Search Report dated May 2, 2007, 2 pages.
International Preliminary Report on Patentability dated Dec. 4, 2011 in application PCT/US2009/058788_7pgs.

* cited by examiner

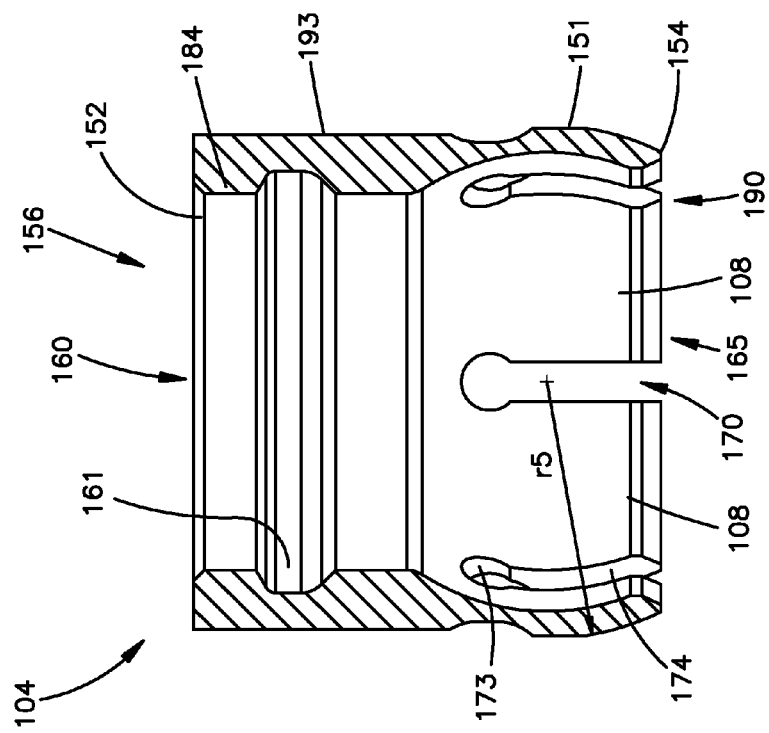
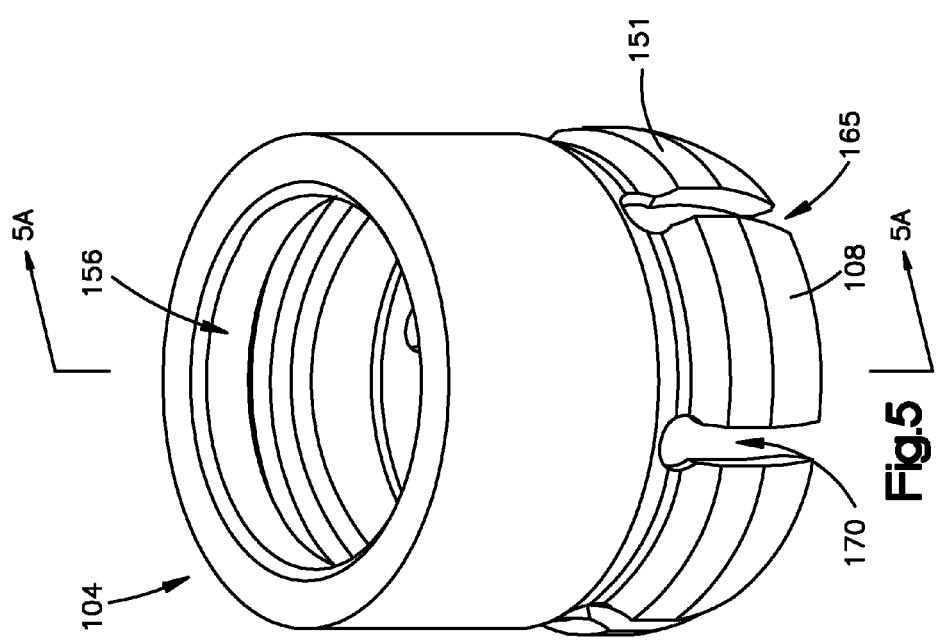
Fig.5A
Fig.5

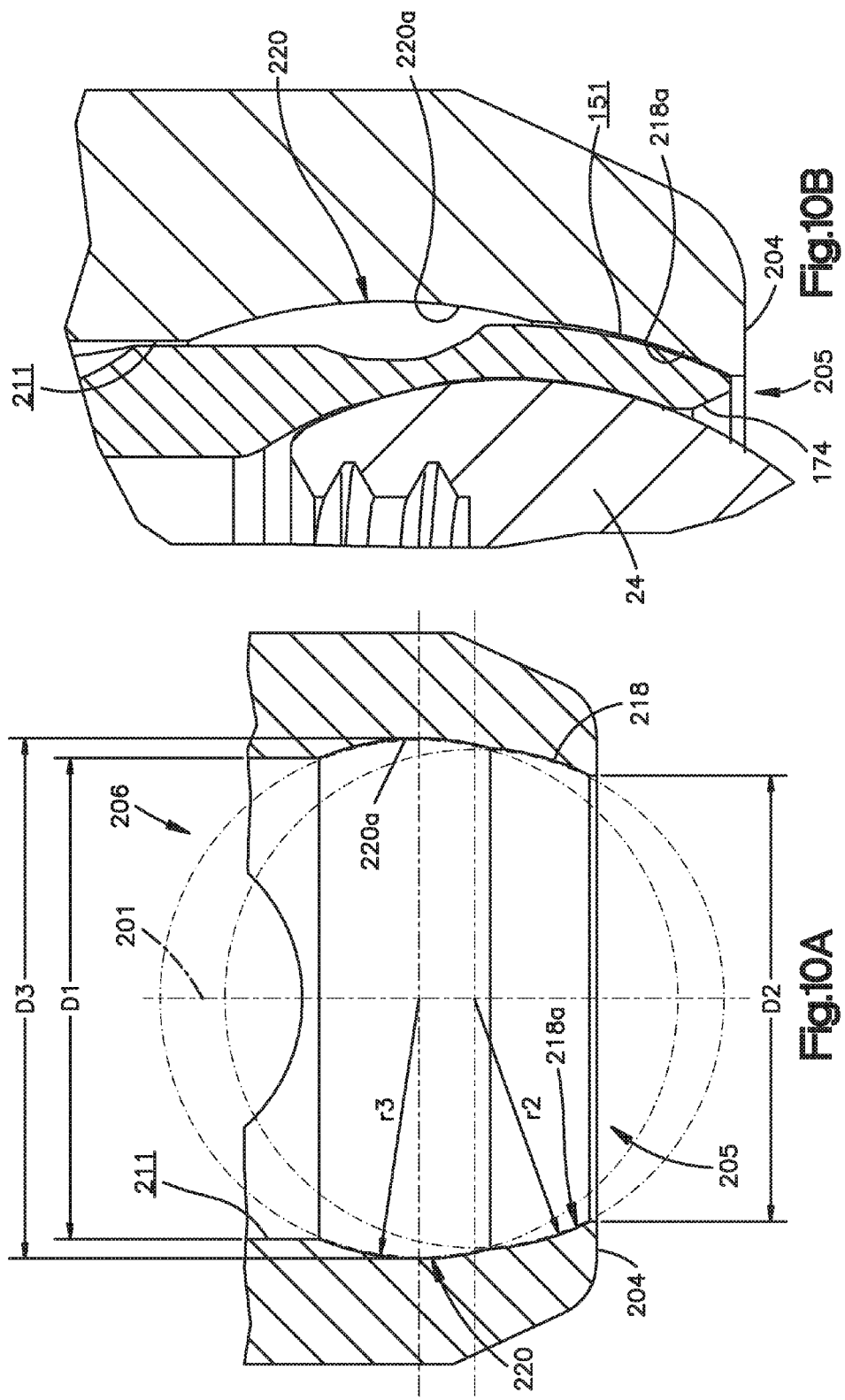

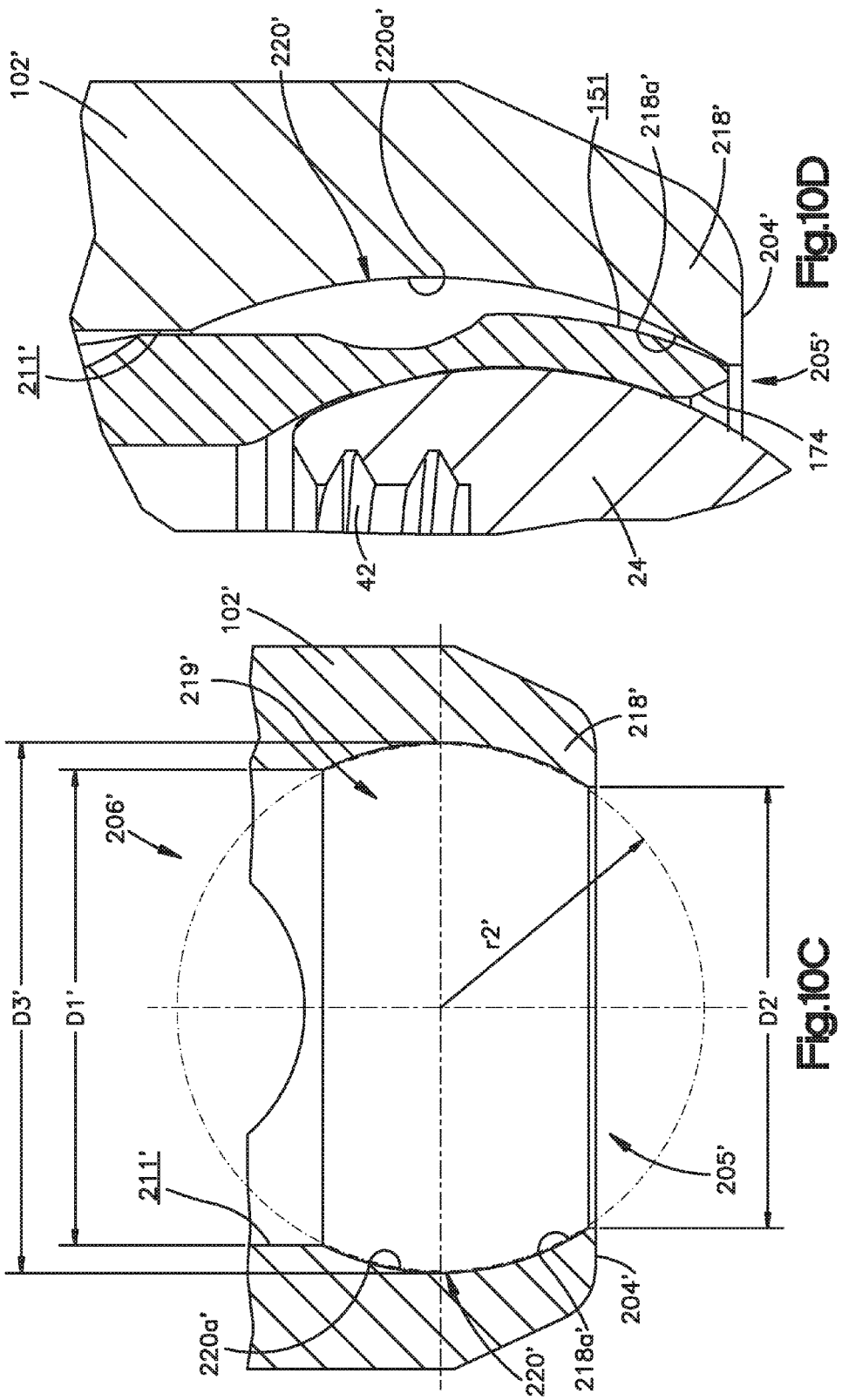

POLYAXIAL BOTTOM-LOADING SCREW AND ROD ASSEMBLY

CROSS REFERENCE TO RELATED APPLICATIONS

This application is continuation application of U.S. patent application Ser. No. 13/121,549, filed Jun. 9, 2011, which is the National Stage of International Application No. PCT/US2009/058788, filed Sep. 29, 2009, which claims the benefit of U.S. Provisional Patent Application No. 61/100,843, filed Sep. 29, 2008, the disclosures of all of which are hereby incorporated by reference as if set forth in their entirety herein.

FIELD OF THE INVENTION

The present invention relates generally to orthopedics. More specifically, the present invention relates to a bone fixation system including a bone fixation assembly having an integrated spinal rod and an associated method for implanting the bone fixation system and assembly.

BACKGROUND OF THE INVENTION

Various spinal disorders are corrected by surgical implants, systems and methods to correct and stabilize spinal curvatures or to facilitate fusion. Numerous implants, systems and methods for treating spinal disorders have been disclosed.

One method involves mounting a pair of spinal rods to the posterior spine on either or both sides of the spinous processes of the vertebral column. Each rod is attached to various vertebrae along the length of the spine by pedicle screws. The body portion of the pedicle screw includes a rod receiving channel and receives a locking cap to secure the spinal rod to the pedicle screw.

To facilitate insertion of the spinal rod into the rod-receiving channels, polyaxial pedicle screws have been developed. It is desirable to develop a pedicle screw that is simple for a surgeon to use and is able to securely mount the rod to the selected vertebra.

SUMMARY OF THE INVENTION

A preferred embodiment of the present invention is directed to an anchor assembly for use in a spinal fixation procedure. The anchor assembly preferably includes a bone anchor having an enlarged head portion (e.g., a bone screw), a collet (e.g., an insert member), a body portion having an axial bore for receiving the collet and the enlarged head portion of the bone anchor, and a locking cap engageable with the body portion. The locking cap is movable from an unlocked position to a locked position. The body portion preferably includes threads for threadably receiving the locking cap (e.g., an externally threaded set screw). The body portion preferably further includes an integral rod portion which extends from the body portion substantially perpendicular to the longitudinal axis of the body portion. The rod portion is capable of being received by a rod-receiving channel of another bone fixation element, such as the "Polyaxial Bone Fixation Element" disclosed in International Patent Application No. PCT/US2008/070670, filed Jul. 21, 2008, the entire contents of which is incorporated by reference herein.

The anchor assembly preferably enables in-situ assembly. That is, the anchor assembly is preferably configured so that in use, the bone anchor may be secured to the patient's vertebra prior to being received within the body portion. Accordingly, the anchor assembly preferably enables a surgeon to implant the bone anchor without the body portion and collet to maximize visibility and access around the anchoring site. Once the bone anchor has been secured to the patient's vertebra, the body portion can "pop-on" to the bone anchor. The bone anchor may also include an instrument interface so that a surgical instrument can be directly coupled to the bone anchor.

In one preferred embodiment, the anchor assembly includes a bone anchor, a body portion with an integral elongated longitudinal member (e.g., a rod portion) protruding laterally therefrom, a collet, and a locking cap. The bone anchor preferably includes an enlarged, curvate head portion, wherein the head portion includes a first tool interface for engaging a first surgical instrument operatively associated with the bone anchor. The body portion preferably includes a longitudinal axis, an upper end with an upper opening, a lower end with a lower opening, a bore extending between the upper opening and the lower opening wherein the bore has a first diameter, and the integrated longitudinal elongated member. The body portion preferably also includes a lower edge portion adjacent the lower opening. The lower edge portion has a second diameter smaller than the first diameter. The body portion also has a first spherical surface and a second spherical surface disposed between the first and second diameters. The first spherical surface is proximate the lower edge portion and has a radius of curvature.

The collet preferably includes a first end, a second end, and one or more slots extending from the second end, wherein the slots define a plurality of flexible arms. The flexible arms of the collet have an outer spherical surface having a radius of curvature, wherein the radius of curvature of the outer spherical surface of the collet is different than the radius of curvature of the lower edge portion of the first spherical surface. The collet is movably positionable within the bore of the body portion. The locking cap is preferably movably engageable with the body portion. The locking cap is engageable with the body portion and movable from an unlocked position to a locked position, wherein movement of the locking cap from the unlocked position to the locked position urges the flexible arms of the collet against the first spherical surface of the body portion to secure a position of the bone anchor relative to the body portion. This also causes the flexible arms of the collet to come substantially into line contact with at least a portion of the first spherical surface.

In another preferred embodiment, the anchor assembly includes a body portion sized and configured to snap onto a head portion of an implanted bone anchor. The body portion preferably includes a longitudinal axis, an upper end with an upper opening, a lower end with a lower opening, a bore extending between the upper and lower openings wherein the bore has a first diameter, and an integral rod portion that extends from the body portion substantially perpendicular to the longitudinal axis. The bore preferably includes a lower edge portion terminating proximate the lower end and an enlarged diameter portion disposed adjacent to the lower edge portion and between the lower edge portion and the upper end. The lower edge portion preferably has a second diameter while the enlarged diameter portion has a third diameter, wherein the third diameter is preferably larger than the first diameter. The first diameter preferably is larger than the second diameter. The collet preferably includes a first end, a second end, and at least two slots extending from the second end, wherein the slots define a plurality of flexible arms. The flexible arms preferably each have a root end, a terminal end, and a generally spherical, external surface proximate the terminal end. The flexible arms render the collet expandable to accept the head of the bone anchor and compressible to secure the head of the bone anchor relative to the collet. The flexible arms are preferably positioned proximate the enlarged diameter portion in a loading position and at least a portion of the external surface of the flexible arms contact the lower edge portion in a locked position. The collet is preferably movably positionable within the bore of the body portion.

In an alternate preferred embodiment, the anchor assembly preferably includes a bone anchor, a body portion, and a collet. The bone anchor preferably includes a head portion, wherein the head portion includes a drive surface for engaging a first surgical instrument operatively associated with the bone anchor. The body portion preferably includes a longitudinal axis, an upper end with an upper opening, a lower end with a lower opening, a bore extending between the upper and lower openings, and a rod portion integrally extending from the body portion for linking the anchor assembly to a second bone fixation element having a rod-receiving channel. The integral rod preferably is oriented substantially perpendicular to the longitudinal axis of the body portion. The bore preferably also includes a lower edge portion proximate the lower end and an enlarged diameter portion proximate to the lower edge portion and between the lower edge portion and the upper end. The lower edge portion is associated with a first spherical surface and the enlarged diameter portion has a second spherical surface. The collet is preferably movably positionable within the bore of the body portion. The collet preferably includes a first end, a second end and one or more slots extending from the second end, wherein the slots define flexible arms. The flexible arms preferably render the collet expandable to accept the head of the bone anchor and compressible to secure the head of the bone anchor relative to the collet. The collet preferably further includes a cavity. The flexible arms of the collet are preferably positioned in general vertical alignment with the enlarged diameter portion in a loading position so that the head of the bone anchor can be received in the cavity formed in the collet. At least a portion of the flexible arms preferably contact the first spherical surface when the locking cap is in a locked position so that the head of the bone anchor is secured with respect to the collet. In the locked position, the contact between the external surface of the flexible arms and the first spherical surface is generally a line contact between the collet and the body portion.

BRIEF DESCRIPTION OF THE SEVERAL VIEWS OF THE DRAWINGS

The foregoing summary, as well as the following detailed description of preferred embodiments of the system described in the application, will be better understood when read in conjunction with the appended drawings. The preferred embodiments of an anchor assembly are shown in the drawings for the purposes of illustration. It should be understood, however, that the application is not limited to the precise arrangements, structures, features, embodiments, instrumentalities, and methods shown and described, and the arrangements, structures, features, embodiments, instrumentalities, and methods shown and described may be used singularly or in combination with other arrangements, structures, features, embodiments, instrumentalities, and methods. In the drawings:

FIG. 5 illustrates a top perspective view of a collet element of the anchor assembly of FIG. 1;

FIG. 5A illustrates a cross-sectional view of the collet element of FIG. 5, taken along line 5A-5A of FIG. 5;

FIG. 10A illustrates a magnified cross-sectional view of a body portion of the anchor assembly of FIG. 1;

FIG. 10B illustrates a magnified cross-sectional view the body portion, the collet element and a head of a screw of the anchor assembly of FIG. 1, taken from within oval 10B of FIG. 2;

FIG. 10C illustrates a magnified cross-sectional view of a body portion of the anchor assembly of FIG. 3; and FIG. 10D illustrates a magnified cross-sectional view of a body portion, a collet element and a head of a screw of the anchor assembly of FIG. 3, taken from within oval 10D of FIG. 3 wherein the collet element and the head of the screw are moved downwardly slightly relative to the body portion.

DETAILED DESCRIPTION OF THE INVENTION

Figure 1:
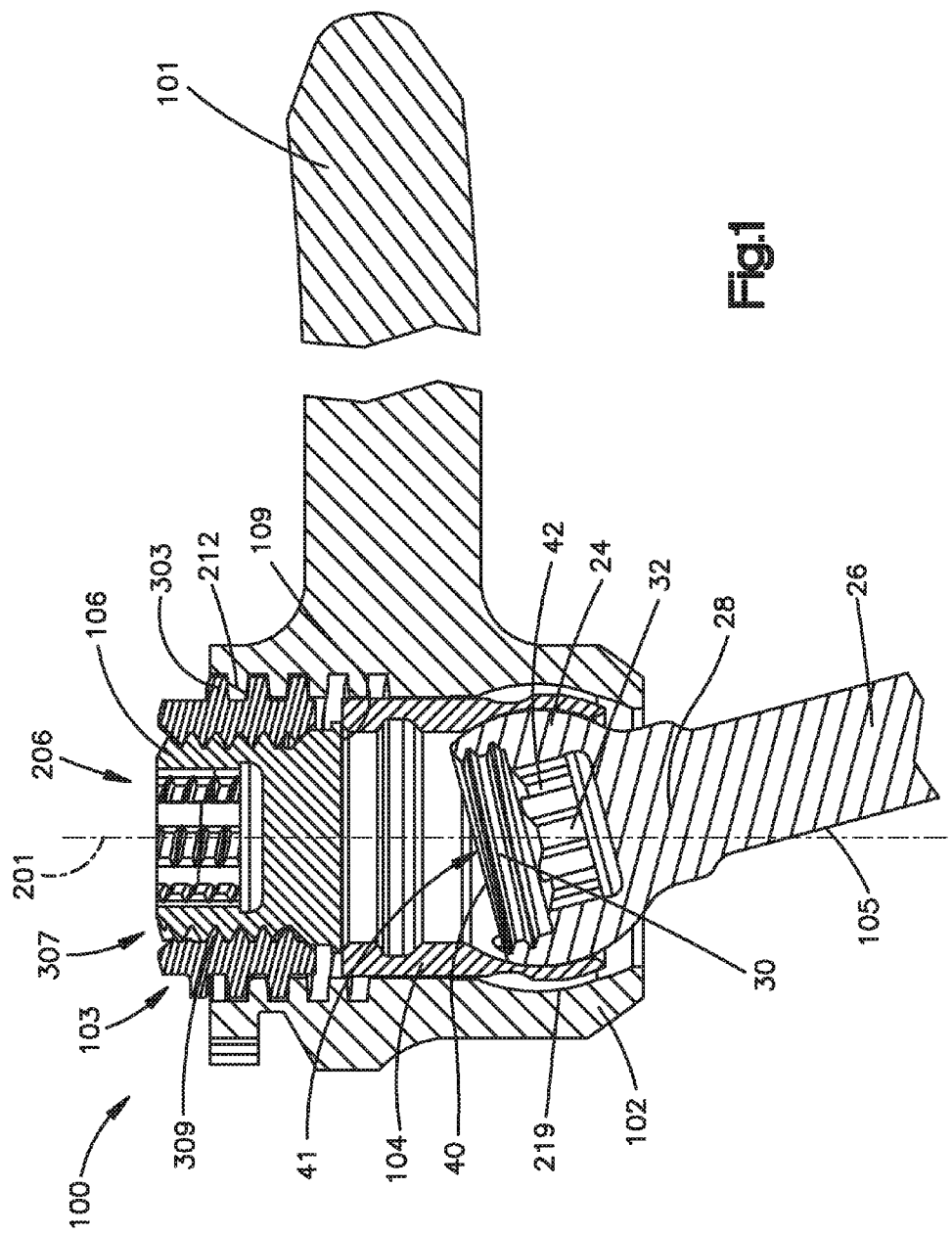
FIG. 1 illustrates a cross-sectional view of a first preferred embodiment of an anchor assembly in an unlocked state taken along line 1-1 of FIG. 4, in accordance with the present invention.

Certain terminology is used in the following description for convenience only and is not limiting. The words "right", "left", "lower", "upper", "top", and "bottom" designate directions in the drawings to which reference is made. The words "inwardly" or "distally" and "outwardly" or "proximally" refer to directions toward and away from, respectively, the geometric center of the anchor assembly, the described instruments and designated parts thereof. The words, "anterior", "posterior", "superior", "inferior", "medial", and "lateral" and related words and/or phrases designate preferred positions and orientations in the human body portion to which reference is made and are not meant to be limiting. The terminology includes the above-listed words, derivatives thereof and words of similar import.

Certain exemplary embodiments of the invention will now be described with reference to the drawings. In general, such embodiments relate to preferred embodiments of anchor assemblies, and related instruments by way of non-limiting example and an anchor assembly for use in spinal fixation that includes an elongated member, typically in the form of a spinal rod portion, that may be integrally and monolithically formed as part of the anchor assembly and which may be inserted into a rod-receiving channel of a second bone fixation element to link and connect the anchor assembly to the second bone fixation element in a bone fixation system preferably for correcting or stabilizing spinal curvatures or to promote fusion of spinal vertebra.

Figure 2:
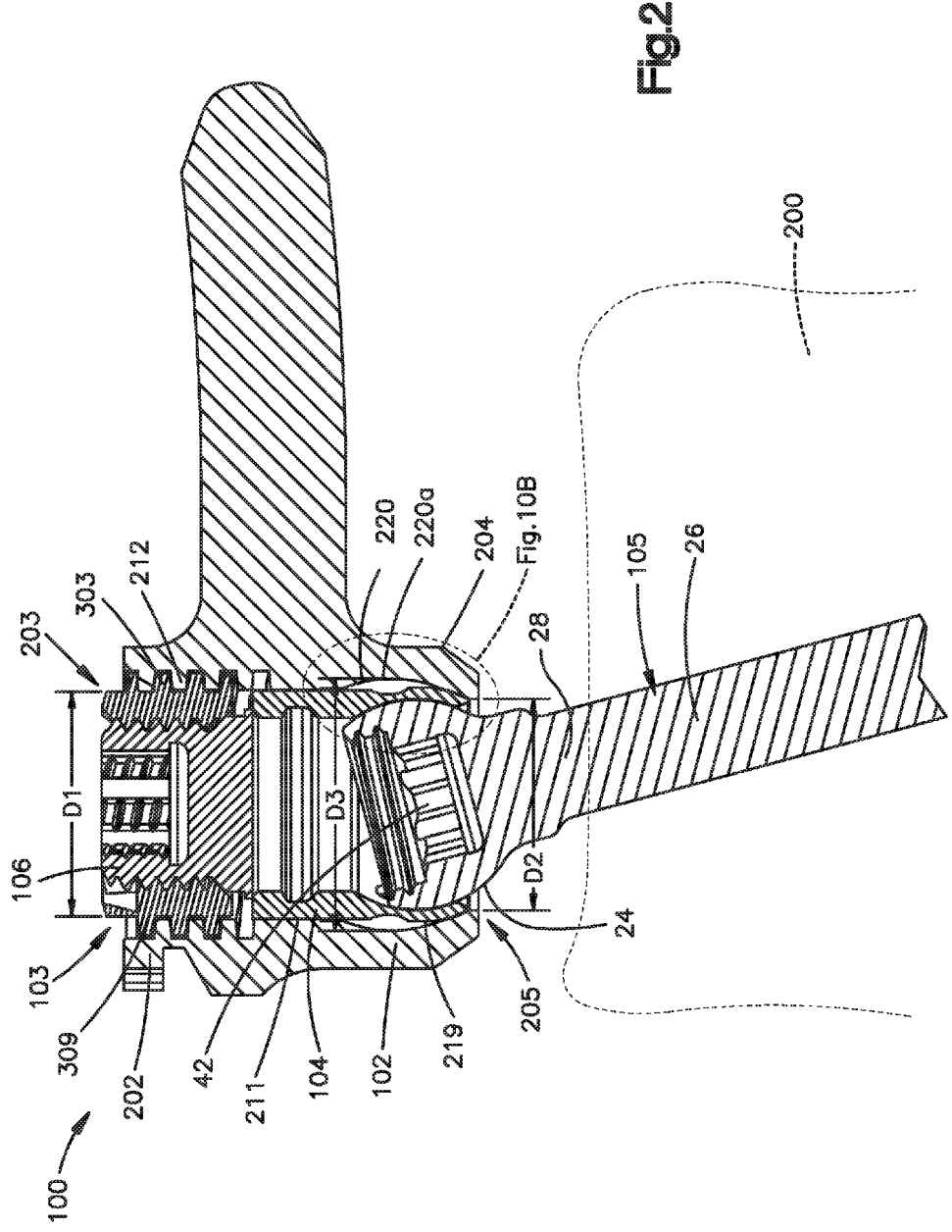
FIG. 2 illustrates a cross-sectional view of the anchor assembly of FIG. 1 in a locked state.
Figure 3:
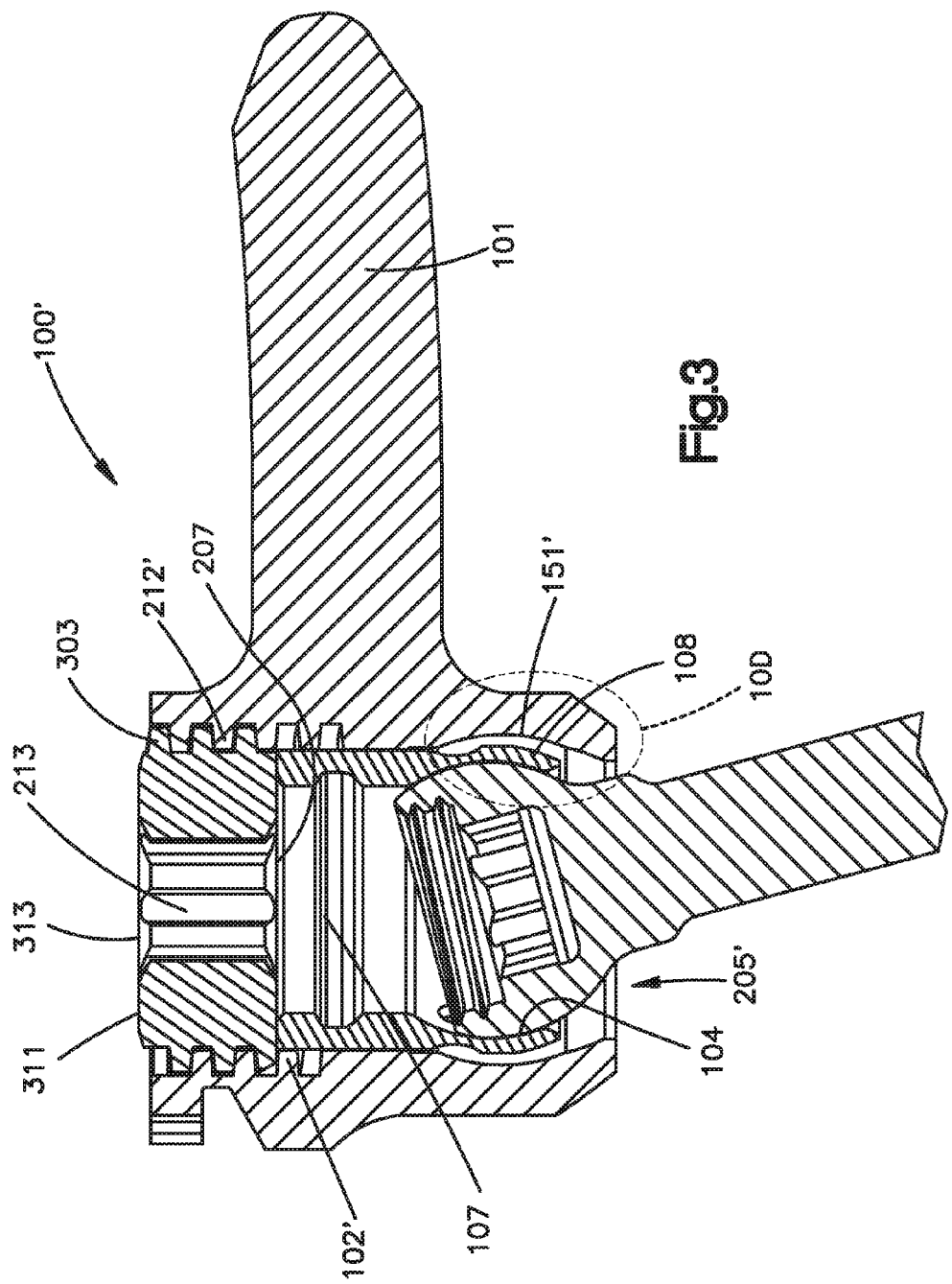
FIG. 3 illustrates a cross-sectional view of a second preferred embodiment of an anchor assembly in an unlocked state in accordance with the present invention.
Figure 4:
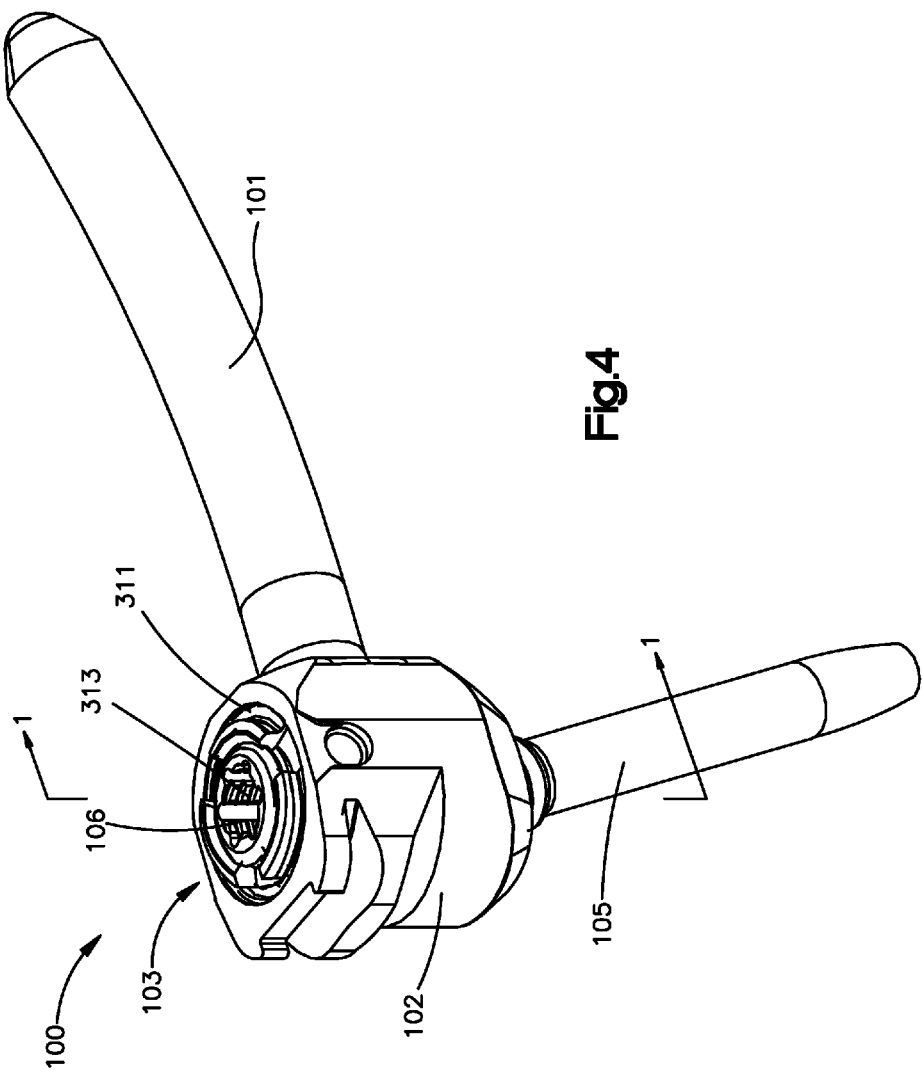
FIG. 4 illustrates a top perspective view of the anchor assembly of FIG. 1.

Referring to FIGS. 1-4A, first and second preferred embodiments of an anchor assembly 100, 100' include a bone anchor 105 (shown as a bone screw), a collet 104, a body portion 102, 102' having a rod portion 101, and a locking cap 103, which, in the first preferred embodiment of FIGS. 1-2 and 4 includes an externally threaded set screw 106. The anchor assemblies 100, 100' preferably enable in-situ assembly of the bone anchor 105 to the body portion 102, 102'. Specifically, the anchor assemblies 100, 100' are configured so that in use, the bone anchor 105 may be secured to a patient's vertebra 200 prior to being received within the body portion 102, 102'. The anchor assemblies 100, 100' preferably enable a surgeon to implant the bone anchor 105 without the body portion 102, 102' and collet 104 pre-assembled to the bone anchor 105. By enabling the surgeon to implant the bone anchor 105 without the body portion 102, 102', the anchor assemblies 100, 100' maximize visibility and access around the anchoring site. Once the bone anchor 105 has been secured to the patient's vertebra 200, the rod portion 101 may be inserted into a second bone fixation element 10 (See FIG. 4A) anchored at a second site, and the body portion 102, 102' and collet 104 may "pop-on" to the bone anchor 105.

Alternatively, the body portion 102, 102' and collet 104 may be popped onto the bone anchor 105 and then the integrated rod portion 101 inserted into the second bone fixation element 10 at a second site. Accordingly, in the preferred anchor assemblies 100, 100', the bone anchor 105 enters the body portion 102, 102' through a lower or bottom end 205, 205' of the body portion 102, 102'. Moreover the integration and preferably monolithic formation of the rod portion 101 into the body portion 102, 102' facilitates a simpler, more efficient procedure as such integration permits the surgeon to fuse several bone fixation elements together without having to implant a separate rod. Alternatively, the anchor assemblies 100, 100' (i.e., body portion 102, 102', collet 104 and bone anchor 105) may be provided pre-assembled using components identical or similar to the components described herein. Further, the assembly of the collet 104 and body portion 102, 102' may be popped-off of the bone anchor 105 in-situ by arranging and positioning the collet 104 in a loading/unloading position relative to the body portion 102, 102', and removing the assembly from the bone anchor 105, as will be described in greater detail below.

While the anchor assembly 100 of the first preferred embodiment will be described as and may generally be used in the spine (for example, in the lumbar, thoracic or cervical regions), those skilled in the art will appreciate that the anchor assembly 100 may be used for fixation of other parts of the body such as, for example, joints, long bones, ribs, or bones in the hand, face, feet, toe, extremities, cranium, mandible, etc.

Figure 4A:
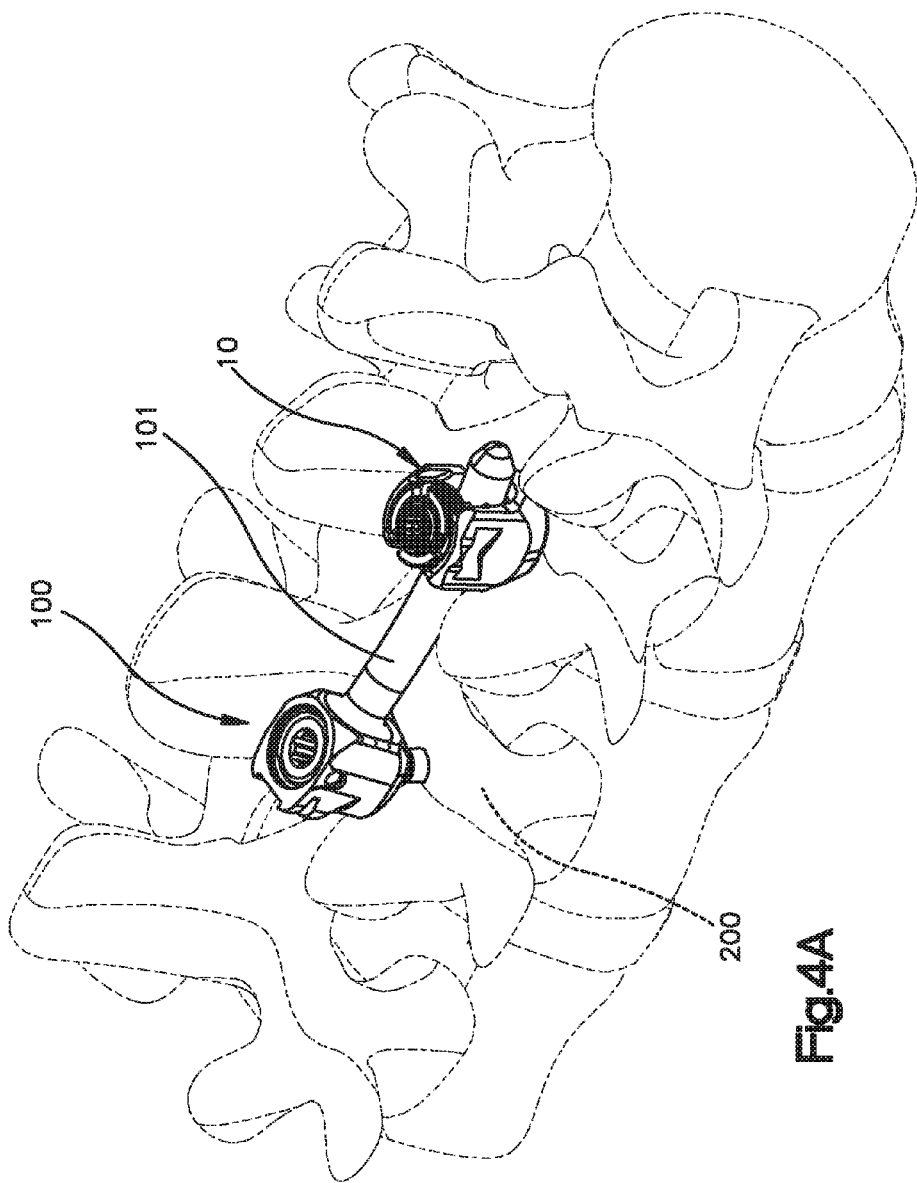
FIG. 4A illustrates a top perspective view of the anchor assembly of FIG. 1 implanted in a vertebra and attached to a second bone fixation element.

As described in greater detail below and illustrated in FIG. 4A, several anchor assemblies 100 and second bone fixation elements 10 having rod-receiving channels may be used to secure and interconnect several vertebrae 200. It should be understood that the spinal rod 101 may constitute or include, but is not limited to, a solid rod, a non-solid or hollow rod, a flexible or dynamic rod, etc. It should be understood that the anchor assemblies 100, 100' of the first and second preferred embodiments are not limited in use to any particular type of spinal rod 101 and may be comprised of any elongated element of any shape and configuration extending from the body portion 102, 102'.

Referring to FIGS. 1-2 and 5-5A, the bone anchor 105 of the first preferred embodiment is in the form of a bone screw or pedicle screw 105. Alternatively, the bone anchor 105 may be, for example, a hook, pin, blade, nail, tack, stake or other fastener such as, a clamp, an implant, etc.

The bone screw 105 preferably includes an enlarged, curvate head portion 24 and an externally threaded shaft portion 26 for engaging the patient's vertebra 200. The specific features of the shaft 26 including, for example, thread pitch, shaft diameter, shaft shape, etc. may be varied, and it would be apparent to one having ordinary skill in the art that the bone screw 105 is not limited to any particular features on or type of shaft 26. The bone screw 105 may or may not be cannulated. The bone screw 105 may also include a reduced diameter neck portion 28 between the head portion 24 and the shaft portion 26, which accommodates the polyaxial nature of the body portion 102 relative to the bone screw 105. The bone screw 105 may further be cannulated and fenestrated (not shown) such that openings extend outwardly from a central hollow channel for a multitude of potential uses, including, but not limited to, urging material out of the screw 105 during injection, drawing fluid into the central hollow channel from sides of the screw 105 to extract material adjacent the screw 105, or passing through instruments or additional implants.

Referring to FIG. 1, the enlarged curvate head portion 24 preferably has a curvate or semi-spherical shape to facilitate pivoting or polyaxial movement of the head portion 24 with respect to the collet 104. The head portion 24 also preferably includes a drive surface 30 for receiving a corresponding tip formed on a drive tool, such as a screw driver (not shown) for rotating the bone screw 105 into engagement with the patient's vertebra 200. The drive surface 30 may have any form now or hereafter known including, but not limited to, an external hexagon, a star drive pattern, a Phillips head pattern, a slot for a screw driver, a threading for a correspondingly threaded post, etc. Preferably, as shown, the drive surface 30 is comprised of a first tool interface or an internal recess 32, but is not so limited and may be comprised of an external drive feature that engages a female-type driver (not shown). The specific shape of the drive surface 30 or first tool interface 32 may be chosen to cooperate with the corresponding drive tool.

As disclosed in International App. No. PCT/US2008/070670, entitled "Polyaxial Bone Fixation Element," filed Jul. 21, 2008, the entire contents of which are incorporated by reference herein, the head portion 24 may also include a second tool interface or a sleeve interface 40. The second tool interface 40 may include threading (as shown) or other features to interact with instruments, such as a drive instrument.

Referring to FIG. 5-5A, the collet 104 preferably includes a lower end portion 154 sized and configured to contact at least a portion of the head portion 24 of the bone anchor 105. The lower end portion 154 of the collet 104 preferably includes an interior cavity 165 for receiving and securing the head portion 24 of the bone anchor 105 so that, as will be generally appreciated by one of ordinary skill in the art, the bone anchor 105 can polyaxially pivot or move through a range of angles with respect to the collet 104 and hence with respect to the body portion 102 when in an unlocked position. The cavity 165 formed in the collet 104 preferably has a curvate or semi-spherical shape for receiving the curvate or semi-spherical head portion 24 of the bone anchor 105 so that the bone anchor 105 can polyaxially rotate with respect to the collet 104, and hence, with respect to the body portion 102. Furthermore, at least a portion of the outer surface of the collet 104 is comprised of a curvate or frusta-spherical, convex surface 151 having a radius of curvature r5 for contacting the inner surface 211 of the body portion 102 (FIG. 2), preferably the lower edge portion 218, or the inner surface 211, as will be described in greater detail below.

The collet 104 preferably also includes one or more slots 170 (shown as a plurality of slots 170) extending from the lower end portion 154 thereof so that at least a portion of the collet 104 is: (i) radially expandable so that the head portion 24 of the bone anchor 105 can be inserted through the lower end portion 154 and into the cavity 165 of the collet 104 and (ii) radially compressible to compress or crush-lock against the head portion 24 of the bone anchor 105, when radial forces are applied thereto. In the preferred embodiments, the slots 170 define a plurality of flexible arms 108. Preferably each flexible arm 108 includes a root end 173 and a terminal end 174. The outer surface of the flexible arms 108 preferably forms at least a portion of the curvate or frusta-spherical convex surface 151 of the collet 104.

The collet 104 also includes a bore 156 extending from an upper opening 160 at the upper end 152 to the lower end 154 so that, for example, a drive tool, such as, for example, a screw driver (not shown), can be inserted through the collet 104 and into engagement with the bone anchor 105 so that the bone anchor 105 may be rotated into engagement with the patient's vertebra 200.

The collet 104 is permitted to move within the axial bore 206 formed in the body portion 102 between a loading/unloading/unlocked position (FIG. 1) and a locked position (FIG. 2). However, the collet 104 is preferably constructed such that it may be inserted into the body portion 102 through the upper opening 203, but is prevented from exiting through the lower opening 205. Once the collet 104 is placed into the body portion 102, the collet 104 is preferably retainable within the body portion 102 such that the collet 104 is generally prevented from either passing back up through the upper opening 203 formed in the body 102 or passing through the lower opening 205 formed in the body 102.

Referring to FIG. 5-5A, the collet 104 includes an inwardly projecting ledge 184 disposed on an inner surface 161 of the collet body 193 adjacent the upper end 152 of the collet 104. The ledge 184 may be engaged by a tool (not shown) to apply a force to the collet 104 to move the collet 104 relative to the body portion 102. For example, when the collet 104, body portion 102, and bone anchor 105 are in the locked position, the body portion 102 may be urged downwardly toward the bone anchor 105 relative to the collet 104 to move the collet 104 from the locked position into the loading position. When the collet 104 is in the loading position, the flexible arms 108 are able to flex outwardly within an enlarged diameter portion 220 to permit the head 24 to move out of the cavity 165. Accordingly, the ledge 184 may be utilized to disassemble the collet 104 and body portion 102 from the bone anchor 105 after the collet 104 and body portion 102 have been locked to the head 24.

Referring to FIGS. 1, 2, 10A and 10B, the body portion 102 may generally be described as a cylindrical tubular body portion having a longitudinal axis 201, an upper end 202 having an upper opening 203, a lower end 204 having a lower opening 205, and an axial bore 206 substantially coaxial with the longitudinal axis 201 of the body portion 102. The axial bore 206 extends from the upper opening 203 to the lower opening 205. The axial bore 206 preferably has a first diameter portion $D_1$ proximate the upper end 202. The inner surface 211 of the axial bore 206 preferably includes a plurality of threads 212 in the upper end 202 for engaging a locking cap 103. Alternatively, the body portion 102 and, in particular, axial bore 206 may have nearly any mounting receiving structure for engaging the locking cap 103 including, but not limited to, external threads, cam-lock, quarter lock, clamps, lugs, bayonets, etc.

Referring to FIGS. 1-3 and 10A-10D, the inner surface 211, 211' of the axial bore 206, 206' of the first and second preferred embodiments also includes a lower end portion 218, 218' proximate the lower end 204, 204' thereof forming a lower chamber 219, 219'. The lower chamber 219, 219' has a second diameter portion $D_2$, $D_2$' at the lower opening 205, 205', which preferably has the smallest diameter portion of the axial bore 206, 206'. The second diameter portion $D_2$, $D_2$' is preferably smaller than the first diameter portion $D_1$, $D_1$' of the axial bore 206, 206' such that the collet 104 may be inserted through the upper end 202, 202' into the axial bore 206, 206', but is prevented from being inserted through or from falling out of the lower opening 205, 205' at the lower end 204, 204'. The second diameter portion $D_2$, $D_2$' is preferably sized and configured so that the enlarged head portion 24 of the bone anchor 105 may be passed through the lower opening 205, 205' of the body portion 102, 102' to be received within the interior cavity 165 of the collet 104.

The lower chamber 219, 219' of the first and second preferred embodiments is defined by a first spherical surface 218a, 218a' adjacent the lower end 204, 204' of the body portion 102, 102'. The first spherical surface 218a, 218a' is preferably defined as a curvate or spherical concave surface for accommodating the outer curvate or spherical convex surface 151 of the collet 104. The first spherical surface 218a, 218a' has a second radius of curvature r2, r2' (shown in FIG. 10A) that preferably is centered on the longitudinal axis 201, 201' of the body portion 102, 102' and is different than the radius of curvature r5 of the spherical convex surface 151 of the collet 104 such that line contact is defined between the outer curvate and first spherical surfaces 151, 218a, 218a' when the collet 104 is positioned proximate the lower end 204, 204' in the locked position.

The inner surface 211, 211' of the axial bore 206, 206' preferably includes an enlarged portion 220, 220' that is located toward the lower end 204, 204' of the body portion 102, 102' between the lower chamber 219, 219' and the upper end 202, 202'. The enlarged portion or second chamber 220, 220' preferably defines a third diameter $D_3$, $D_3$' comprised of a curvate, preferably frusto-spherical, radially outwardly recessed portion. In the enlarged portion 220, 220' of the axial bore 206, 206', the third diameter $D_3$, $D_3$' is larger than the first diameter $D_1$, $D_1$' of the axial bore 206, 206'. In addition, the third diameter $D_3$, $D_3$' is larger than the second diameter $D_2$, $D_2$'.

The enlarged portion 220, 220' preferably accommodates expansion of the flexible arms 108 when the head 24 is loaded into the collet 104. The enlarged portion 220, 220' is preferably in the form of a curvate or frusto-spherical concave interior surface 220a, 220a'. Referring to FIGS. 10A and 10B, in the first preferred embodiment, the interior surface 220a is defined by a third radius of curvature r3, which defines the third diameter $D_3$ at the largest diameter within the axial bore 206. The third radius of curvature r3 defines the spherical nature of the second spherical surface 220a. The third radius of curvature r3 preferably is different from the second radius of curvature r2 and may also, but need not be, different from the radius of curvature r5 of the spherical convex surface 151 of the collet 104. The enlarged portion 220 is sized and configured so that when the collet 104 is placed in the curvate or frusto-spherical concave interior surface of the enlarged portion 220, the flexible arms 108 of the collet 104 are permitted to radially expand a sufficient amount within the axial bore 206 of the body portion 102 so that the head portion 24 of the bone anchor 105 can be inserted into the cavity 165 formed in the collet 104. More preferably, but not necessarily, the enlarged portion 220 is sized and configured so that the outer curvate or frusto-spherical convex surface 151 of the collet 104 preferably does not touch or contact the enlarged portion 220 of the body portion 102 when the head 24 is loaded into the collet 104. That is, the enlarged portion 220 formed in the body portion 102 is preferably sized and configured so that the flexible arms 108 may radially expand sufficiently to accept the head portion 24 of the bone anchor 105. The enlarged portion 220 is not limited to constructions comprised of the preferred curvate or spherical surface defined by the third radius of curvature r3 and may be constructed to have a surface of nearly any shape that permits expansion of the collet 104 in the loading position to accept the head 24. For example, the enlarged portion 220 may be defined by a rectangular slot or groove on the inner surface 211 or a cylindrically shaped chamber that results in the third diameter $D_3$ being larger than the first and second diameters $D_1$, $D_2$.

Referring to FIGS. 10A-10B, in the first preferred embodiment, the second radius of curvature r2 of the first spherical surface 218a is preferably different than an outer radius of curvature r5 of the outer curvate or spherical convex surface 151 of the collet 104 so that generally a line contact results between the first spherical surface 218a and the outer convex surface 151 when the collet 104 is positioned adjacent the lower end portion 218 (FIG. 10B). Because the radii of curvature r2, r5 are not the same, the curvate surfaces do not generally contact along a large surface area, but rather generally along a line or a line of limited thickness or width, forming a generally line contact. That is, by providing non-matching radii of curvature r2, r5 between the first spherical surface 218a and the collet 104, line contact generally occurs between the first spherical surface 218a of the body portion 102 and the outer curvate or spherical convex surface 151 of the collet 104. The generally line contact between the body portion 102 and the collet 104 effectively pinches the lower ends of the flexible arms 108 into the lower end of the head 24 below the greatest diameter of the head 24 so that the lower end 154 of the collet 104 is pressed beneath the largest diameter of the head 24, effectively locking the bone anchor 105 to the collet 104 and placing the collet 104 in the locked position.

Referring to FIGS. 10C-10D, in the second preferred embodiment, the second and third diameters D2', D3' may be formed by a single internal radius of curvature r4' formed in the axial bore 206' of the body portion 102'. The single internal radius of curvature r4' preferably permits insertion of the collet 104 into the axial bore 206' from the upper end 202' but not the lower end 204', prevents the collet 104 from exiting through the lower end 204', permits expansion of the collet 104 to accept the head 24, and permits generally line contact between the outer curvate or spherical convex surface 151 of the collet and the first spherical surface 218a' when the collet 104 is in facing engagement with the lower end portion 218'. In this configuration, the second diameter portion D2' is smaller than the first diameter portion D1', which is smaller than the third diameter portion D3'.

Referring to FIGS. 1-4 and 6-8, the locking cap may preferable be either a two piece locking cap 103 or a single piece locking cap 213. In both preferred embodiments, the locking caps 103, 213 may generally be described as a cylindrical tubular locking cap 103, 213 having external threads 303 for threadably engaging the threads 212, 212' formed on the inner surface 211, 211' of the body portion 102, 102'. The locking cap 103, 213 may additionally be either detachable or undetachable from the body portion 102, 102'. The locking cap 103, 213 may be any locking cap now known or hereafter developed for such purpose including, but not limited to, an externally threaded cap, an internally threaded cap, a quarter-turn or partial-turn locking cap, cam-lock bayonet and lug, two-piece set screw, etc.

As shown in FIGS. 1-2, 4, and 6-8, the two-piece locking cap 103 includes a set screw element 106. The locking cap 103 further includes a bore 307 and interior threads 309 (FIG. 8) disposed on the interior of the locking cap 103 to threadably engage the external threads 701 (FIG. 7) of set screw 106. The locking cap 103 and set screw 106 preferably include drive surfaces 311, 313 (FIG. 4) for engaging corresponding drive tools for securing (e.g., threading) the locking cap 103 and set screw 106 onto the body portion 102. The drive surfaces 311, 313 may take on any form now or hereafter developed for such purpose, including, but not limited to, an external hexagon, a star drive pattern, a Phillips head pattern, a slot for a screw driver, a threading for a correspondingly threaded post, etc. The drive surfaces 311, 313 are each preferably comprised of internal recesses. The specific shape of the internal recess may be chosen to cooperate with the corresponding drive tool. The drive surfaces 311, 313 may also be configured to include the first and second tool interfaces 32, 40, as were described above.

Figure 6:
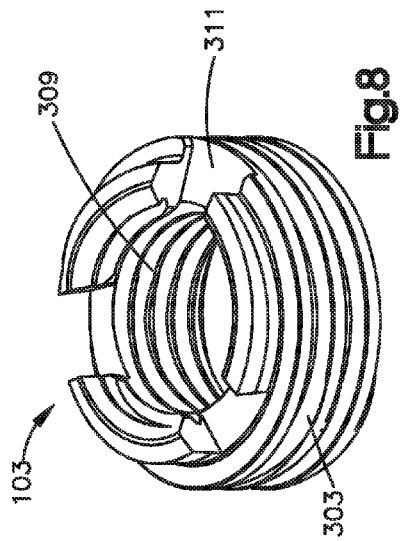
FIG. 6 illustrates a side elevational view of a locking cap and set screw assembly for the anchor assembly of FIG. 1.
Figure 8:
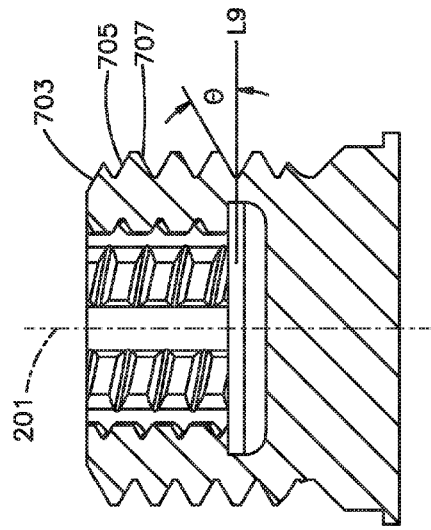
FIG. 8 illustrates a top perspective view of the locking cap element of the assembly of FIG. 6.
Figure 7:
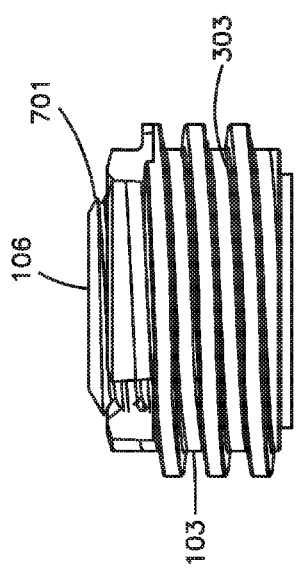
FIG. 7 illustrates a top perspective view of the set screw element of the assembly of FIG. 6.

Alternatively, the two-piece locking cap 103 may have a thread pitch that differs from a thread pitch of threads on the inner surface 211 of the upper end 202 of the body portion 102, as best shown in FIGS. 1-2. Specifically, the thread pitch of at least some of the exterior threads 303 of locking cap 103, as best shown in FIGS. 6 and 8, differ from the thread pitch of at least some of the threads on the inner surface 211 such that the locking cap 103 will bind with the body portion 102 at a predetermined distance, yet is removable from the body portion 102 should it be desired that the anchor assembly 100 be switched out, e.g., for a different size. In such a configuration, the amount of interference experienced between the mating threads as the locking cap 103 progresses downward within the body portion 102 is exponential with respect to the amount of threading mated together. The mismatch between the exterior threads 303 of the locking cap 103 and the threads 212 formed in the body portion 102 is advantageous as this feature enhances the back-out resistance of the assembly due to binding and friction fit of the mismatched threads. Only a portion of the threads 303, 212 may be mismatched where the thread pitch may be about 1.15 mm for the threads 212 formed in the body portion 102 and about 1.0 mm for the threads 303 formed on the locking cap 103. The thread pitch, the thread profile, the difference between the thread pitches, and the portion of the threads that are mismatched, may vary depending on the amount of interference desired.

The single locking cap 213 preferably does not include a set screw element, as best seen in FIG. 3. The single locking cap 213 may likewise include drive surfaces 311, 313 for engaging corresponding drive tools for securing (e.g., threading) the locking cap 213 onto the body portion 102.

Alternatively, the single locking cap 213 may also be provided wherein the thread pitch of threads on the inner surface 211 of the upper end 202 of the body portion 102, as best shown in FIGS. 1-2, differs from the thread pitch of the exterior threads 303 of locking cap 213 (FIG. 3). Thus, the same principal of a mismatch between the exterior threading of the locking cap 103 and the interior threading of the body portion 102 can be utilized with the single locking cap element without a set screw (e.g., FIG. 3), as discussed above with respect to the two piece locking cap 103.

The locking cap 103, 213 may be preassembled and generally undetachable from the body portion 102, eliminating the necessity of assembling the locking cap 103, 213 to the body portion 102 intraoperatively, saving a surgical step, preventing the likelihood of cross-threading between the locking cap 103, 213 and the body portion 102, and eliminating the chance of dropping or losing the locking cap 103, 213 within or near the surgical site. Rendering the locking cap 103, 213 undetachable from the body portion 102 may be accomplished in a number of ways, including, but not limited to, adding a projecting ledge around the circumference of the axial bore 206 of the body portion 102 or including a retaining element at the base of the locking cap 103, 213, which may be engagable with either the threads 212 of the body portion 102 or with a second retaining element disposed on the interior wall of body 102. Alternatively or additionally, the threads 212 of the body 102 matable with the threads 303 of the locking cap 103, 213 may be damaged in a way to prevent the locking cap 103, 213, from coming detached from the body portion 102. Having a locking cap 103, 213 that is undetachable from the body portion 102 is permitted by the integral rod portion 101 and the bottom-loading configuration of the bone anchor 105 so that the surgeon generally does not need to manipulate the bone anchor 105 through the upper opening 203 of the bore 206 of the body portion 102, or implant a spinal rod after attachment of the bone anchor and anchor assembly to the vertebrae 200.

The locking cap 103 may be detachable from the body portion 102 so as to allow the surgeon to gain access to a removal feature (not shown) on the collet 104 to uncouple the collet 104 from the head 24 of the bone anchor 105 and remove the anchor assembly 100 from the bone anchor 105 in the case where the surgeon decides to remove the anchor assembly from the patient, for example when a different style anchor assembly 100 is desirable, e.g., one with a longer or shorter body portion 102 or rod portion 101, etc.

Figure 9:
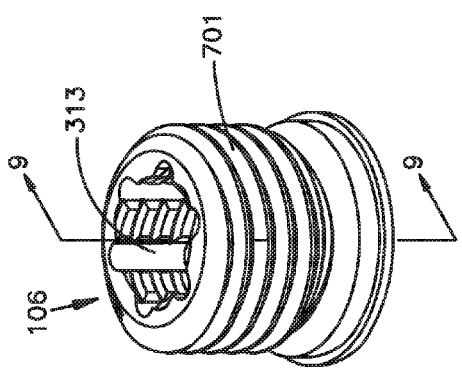
FIG. 9 illustrates a cross-sectional view of the set screw element of FIG. 7, taken along line 9-9 of FIG. 7.

Referring to FIGS. 3 and 9, the exterior threads 303 formed on the locking cap 103, 213 for engaging the threads 212 formed on the body portion 102 (FIG. 2) may incorporate inclined load flanks 703 forming an angle θ with respect to a line L9 perpendicular to the longitudinal axis 201 of the body portion 102. The load flanks 703 may be converging so that the top surface 705 of the thread 303 and the bottom surface 707 of the thread 303 converge. The angle θ may be about five degrees (5°), although, as will be generally appreciated by one of ordinary skill in the art, the threads may take on any other form or angle now or hereafter known for such purpose including, negative load threads, perpendicular threads flanks, buttress threads, etc.

In operation, the threaded shaft 26 of the bone anchor 105 is inserted into bone, preferably the pedicle of the vertebral body 200 or the sacrum, using an instrument such as a driver or power tool (not shown) that interfaces with the drive surface 30 at the proximal end of the bone anchor 105. The integral rod portion 101 may then be inserted into the rod-receiving channel of a second pedicle screw 10 or hook assembly previously implanted at a second site. The body portion 102 is then snapped over the head 24 of the bone anchor 105 as the collet 104 expands to accept the head 24 of the bone anchor 105. Alternatively, the rod portion 101 may be inserted into the rod-receiving channel of the second pedicle screw 10 or hook assembly after the body portion 102 is snapped over the head 24 of the bone anchor 105. The integration of the rod portion 101 with the body portion 102 permits the surgeon to fuse two or more bone fixation elements together and eliminates the need for the surgeon to implant separate spinal rods (not shown) to link the bone fixation elements together.

More specifically, when popping the body portion 102 into the head 24 of the bone anchor 105, the head portion 24 of the bone anchor 105 moves the collet 104 into alignment with the enlarged portion 220 as the head portion 24 is inserted through the lower opening 205 and into the axial bore 206. With the collet 104 positioned within the curvate or spherical concave surface 220a of the enlarged portion 220 in the loading position, which preferably enables the flexible arms 108 of the collet 104 to radially expand within the axial bore 206 of the body portion 102, the head portion 24 of the bone anchor 105 is inserted through the lower opening 205 formed in the body portion 102 and into the cavity 165 formed in the collet 104.

To permit the surgeon to adjust the orientation of the anchor assembly 100, the rod portion 101 may be movably retained in the rod receiving channel of the second pedicle screw 10. To do so, the locking cap of the second pedicle screw 10 may be provisionally engaged such that the rod is captured in the body portion of the second pedicle screw 10 but may move to a certain extent and has limited constraint in the longitudinal direction. The body portion of the second screw 10 may also remain free to move with respect to the screw (not shown) of the second peridcle screw 10. The rod portion 101 also may be retained in the rod receiving channel of the second pedicle screw 10 by other means that retains the rod 101 in the body portion of the second pedicle screw 10 but permits the rod 101 to be adjustably movable. With the rod portion 101 attached to the second bone fixation element 10 and the head 24 positioned in the cavity 165 of the collet 104, the head portion 24 of the bone anchor 105 and the collet 104 are both preferably constrained within the body portion 102 and the bone anchor 105 is preferably able to polyaxially rotate with respect to the collet 104 and the body portion 102 in this configuration. The surgeon may then apply adjustments as required before locking the rod portion 101 into the second pedicle screw 10 or hook assembly or locking the anchor assembly 100. The orientation of the anchor assembly 100 may be adjusted by angulating the bone anchors 105 in the body portion of the anchor assembly 100. When the necessary adjustments to the anchor assembly 100 or the second pedicle screw 10 or hook assembly have been applied, the surgeon may lock the anchor assembly 100 and the second pedicle screw 10 or hook assembly in any desired sequence.

To lock the anchor assembly 100, the locking cap 103, 213 is threaded into engagement with threads 212 formed in the body portion 102. When utilizing the two-piece locking cap 103, the set screw 106 is preferably threaded into engagement with the interior threads 309 of locking cap 103. The bottom surface 109 of the set screw 106 (FIG. 1) or the bottom surface 207 of the locking cap 213, engages the top surface 107 of the collet 104 and applies a downward force to the top surface 107 of the collet 104 as the set screw 106 or locking cap 213 is rotated, thereby causing the collet 104 to move downward, causing contact between the exterior surface 151 of the arms 108 and the first spherical surface 218a of the body portion 102. As the collet 104 is moved further down relative to the body portion 102, the collet 104 contacts the first spherical surface 218a, which causes a radial inward force to be applied to the flexible arms 108, which in turn causes the flexible arms 108 to compress against the head portion 24 of the bone anchor 105, thereby securing the position of the bone anchor 105 with respect to the collet 104 and hence with respect to the body portion 102. The lower end portion 218 and the outer curvate or spherical convex surface 151 of the collet 104 preferably have non-matching radii of curvature r2/r4, r5 so that generally line contact (or contact of limited width) occurs between these components. The preferred line contact between the collet 104 and body portion 102 proximate the terminal ends 174 direct the radial inward force on the flexible arms 108 at a location preferably below the largest diameter of the head 24 to efficiently urge the terminal ends 174 beneath the curved outer surface of the head 24 in the locked position.

The rod portion 101 is then secured within the rod-receiving portion of the second bone fixation element 10 or hook assembly, e.g., by advancing a locking cap or set screw in the second pedicle screw 10. The rod portion 101 may also be secured in the second bone fixation element 10 before locking the anchor assembly 100.

Referring to FIGS. 1-5, the collet 104 and body portion 102 may be popped-off of the bone anchor 105, in situ, after the anchor assembly 100 is engaged in the locked configuration. Specifically, the locking cap 103, 213 of the anchor assembly 100 may be removed from the body portion 102 and the rod portion 101 may be disengaged and extracted from the rod-receiving channel of the second pedicle screw 10. These steps may be executed in any desired sequence. A tool (not shown) engages the ledge 184 of the collet 104 and the body portion 102 and applies a force to the collet 104 to move the body portion 102 downwardly toward the bone anchor 105. The generally line contact between the body portion 102 and the collet 104 is released and the collet 104 is urged upward with respect to the body portion 102 so that the collet 104 is in the loading position. In the loading position, the flexible arms 108 can flex outwardly within the enlarged portion 220 to permit popping-off of the body portion 102 and collet 104 from the head 24 of the bone anchor 105. While the collet 104 and body portion 102 may be removed from the bone anchor 105 as described, their release from the bone anchor 105 is generally non-destructive. The collet 104 and body portion 102 may be reapplied to the bone anchor 105, if desired.

The anchor assembly 100 may form a single level construct, such that a pair of anchor assemblies 100 and second bone fixation elements 10 are arranged in parallel, posteriorly between a pair of vertebral bodies 200, e.g., to assist with a fusion procedure, or alternately, the anchor assembly 100 may couple to a more complex construct, such as, for example, a multi-level construct. The anchor assembly 100 may also couple transversely to a complex construct, such as in serving as a trans-iliac or trans-sacral extension.

The second pedicle screw assembly 10 may be another bottom-loading snap-on body and bone anchor assembly or may be a top-loading assembly or may be any other type of pedicle screw assembly that is capable of receiving the integrated rod portion 101 of the anchor assembly 100. The second pedicle screw assembly 10 may further be monoaxial or a polyaxial pedicle screw assembly or can be a lamina hook with a rod-receiving portion.

The anchor assembly 100 is preferably provided to the user in a kit including (1) bone anchors 105, (2) locking caps 103, 213, (3) pre-assembled collet 104/body portion 102 subassemblies (with integral rod portion 101), and (4) may also optionally include second bone fixation elements 10 with rod receiving channels. The pre-assembled collet/body portion subassemblies are preferably assembled by inserting the collet 104 into the axial bore 206 formed in the body portion 102 through the upper opening 203 formed in the body portion 102. The flexible arms 108 may flex inwardly as the collet 104 is inserted into the axial bore 206, if the greatest diameter of the flexible arms 108 is larger than the first diameter D1. Such a configuration generally results in the collet 104 being retainable within the axial bore 206.

The kit is preferably delivered to the user for use in spinal surgery. During surgery, the surgeon preferably identifies the vertebrae 200 of the spine where the surgery will take place, makes an incision to expose the selected area and implants one or more bone anchors 105, and one or more second bone fixation elements 10 having a rod receiving channel into the desired vertebrae 200. The rod portion 101 is inserted into the rod receiving channel of the second bone fixation element 10 implanted at the second site (FIG. 4a) and then the body portion/collet subassembly is preferably popped-on to the bone anchor 105 by urging the head 24 through the lower opening 205. Alternatively, the body/collet subassembly can be popped onto the bone anchor 105 and then the rod portion 101 is inserted into the rod receiving channel of the second bone fixation element 10. Accordingly, the collet/body portion subassembly may be engaged with the head portion 24 of the bone anchor 105 in situ.

The anchor assembly 100 including the bone anchor 105, the collet 104, the body portion 102 and the locking cap 103 may be made from any biocompatible material now or hereafter known including, but not limited to, metals such as, for example, titanium, titanium alloys, stainless steel, cobalt chromium, Nitinol, etc. Other materials such as, for example, composites, polymers, ceramics, and any other materials now known or hereafter discovered may be used for the anchor assembly, its component parts, and spinal rods.

As will be appreciated by those skilled in the art, any or all of the components described herein may be provided in sets or kits so that the surgeon may select various combinations of components to perform a fixation procedure and create a fixation system which is configured specifically for the particular needs/anatomy of a patient. It should be noted that one or more of each component may be provided in a kit or set. In some kits or sets, the same device may be provided in different shapes and/or sizes.

While the foregoing description and drawings represent the preferred embodiment of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the appended claims.

The invention claimed is:

1. A method of performing spinal fixation, the method comprising steps of:
   implanting a bone anchor of a bone anchor assembly into a first vertebra;
   implanting a bone fixation element having a rod-receiving channel into a second vertebra, spaced from the first vertebra along a first direction, such that a longitudinal axis of the rod-receiving channel extends along the first direction; and
   coupling a body portion of the bone anchor assembly to the bone anchor and the bone fixation element such that (i) a head of the bone anchor is disposed in a bore of the body portion that extends through the body portion from an upper end of the body portion to a lower end of the body portion in a distal direction, and (ii) a fixation rod that is monolithic with the body portion is disposed in the rod-receiving channel of the bone fixation element,
   wherein the coupling step comprises (1) receiving the head of the bone anchor in a collet that is disposed in the bore of the body portion in a loading position such that a plurality of arms that extend from a lower end of the collet toward an upper end of the collet radially expand so as to receive the head of the bone anchor and the plurality of arms are in vertical alignment with an enlarged portion of the bore that has a radius of curvature, and (2) moving the collet with the head within the bore to a locked position such that at least a portion of the flexible arms contact a lower spherical surface of the bore that is offset from the enlarged portion in the distal direction and that has a radius of curvature that is less than the radius of curvature of the enlarged portion.

2. The method of claim 1, wherein the coupling step comprises inserting the fixation rod into the rod-receiving channel before receiving the head of the bone anchor in the bore of the body portion.

3. The method of claim 1, wherein the coupling step comprises receiving the head of the bone anchor in the bore of the body portion before inserting the fixation rod into the rod-receiving channel.

4. The method of claim 1, further comprising a step of attaching a locking cap to the bone fixation element so as to secure the fixation rod in the rod-receiving channel.

5. The method of claim 1, wherein upon receiving the head of the bone anchor in the bore of the body portion, the bone anchor is polyaxially pivotable relative to the body portion, and the method further comprises a step of attaching a locking cap to the body portion such that the locking cap fixes a position of the bone anchor.

6. The method of claim 1, comprising moving the collet from a loading position within the body portion, wherein the bone anchor is polyaxially pivotable relative to the body portion, to a locked position, wherein a position of the bone anchor is fixed relative to the body portion.

7. The method of claim 6, wherein, in the locked position, the collet contacts an inner surface of the body portion causing the plurality of arms to compress against the head of the bone anchor.

8. The method of claim 1, wherein the coupling step comprises receiving the fixation rod in the rod-receiving channel of the bone fixation element between a pair of arms of the bone fixation element that define the channel therebetween.

9. A body portion for a bone anchor assembly, the body portion comprising:
   an upper end defining an upper opening, and a lower end spaced from the upper end along a first direction, the lower end defining a lower opening configured to receive a head of a bone anchor therethrough, the body portion defining a bore that extends through the body portion from the upper opening to the lower opening along a central axis that extends in the first direction, the bore having an enlarged portion, and a lower spherical surface that is spaced from the enlarged portion along the distal direction, the enlarged portion having a radius of curvature that is greater than a radius of curvature of the lower spherical surface, and at least a portion of the bore having a diameter that is greater than a diameter of the lower opening such that the body portion is configured to retain a collet within the bore between the upper end and the lower end; and
   an elongate rod that is monolithic with the body portion and extends from the body portion along a direction that is angularly offset with respect to the central axis, the elongate rod having a length that is sized to extend from a first vertebra to a second vertebra, and the elongate rod being configured to be received in a rod-receiving channel of a bone fixation element.

10. The body portion of claim 9, wherein the body portion is devoid of a rod-receiving channel that extends through the body portion between the upper end and the lower end.

11. The body portion of claim 9, wherein the body portion includes an inner surface that at least partially defines the bore, and the inner surface defines internal threading configured to threadedly engage a locking cap.

12. The body portion of claim 9, wherein the elongate rod extends from the body portion along a direction that is perpendicular to the first direction.

13. The body portion of claim 9, wherein the elongate rod is configured to be received in the rod-receiving channel of the bone fixation element between a pair of arms of the bone fixation element that define the channel therebetween.

14. A bone anchor assembly comprising:
   the body portion of claim 9; and
   a collet configured to be retained in the bore of the body portion, the collet defining an upper end, and a lower end spaced from the upper end of the collet along the first direction, the lower end configured to expand so as to receive the head of the bone anchor.

15. The bone anchor assembly of claim 14, wherein the collet is movable within the bore from an unlocked position, wherein the bone anchor is polyaxially pivotable relative to the body portion, to a locked position, wherein a position of the bone anchor is fixed relative to the body portion.

16. The bone anchor assembly of claim 15, wherein the collet is configured such that, in the locked position, the collet contacts an inner surface of the body portion causing the lower end of the collet to compress against the head of the bone anchor.

17. The bone anchor assembly of claim 15, further comprising a locking cap configured to engage internal threads of the bore of the body portion, wherein movement of the locking cap within the bore causes movement of the collet from the unlocked position to the locked position.

18. The bone anchor assembly of claim 15, wherein the elongate rod extends from the body portion along a longitudinal axis that is perpendicular to the central axis, and the longitudinal axis extends through the collet when the collet is in at least one of the unlocked position and the locked position.

* * * * *